(12) United States Patent
Fahmy et al.

(10) Patent No.: US 9,921,216 B2
(45) Date of Patent: *Mar. 20, 2018

(54) NANOELECTRONIC-ENZYME LINKED IMMUNOSORBENT ASSAY SYSTEM AND METHOD

(71) Applicant: Yale University, New Haven, CT (US)

(72) Inventors: Tarek M. Fahmy, New Haven, CT (US); Eric D. Stern, New Haven, CT (US); Mark A. Reed, Monroe, CT (US); Aleksandar Vacic, New Haven, CT (US); James F. Klemic, Falls Church, VA (US)

(73) Assignee: Yale University, New Haven, CT (US)

( * ) Notice: Subject to any disclaimer, the term of this patent is extended or adjusted under 35 U.S.C. 154(b) by 267 days.

This patent is subject to a terminal disclaimer.

(21) Appl. No.: 14/755,615

(22) Filed: Jun. 30, 2015

(65) Prior Publication Data
US 2016/0054315 A1 Feb. 25, 2016

Related U.S. Application Data

(60) Division of application No. 12/535,396, filed on Aug. 4, 2009, now Pat. No. 9,188,594, which is a
(Continued)

(51) Int. Cl.
*G01N 33/543* (2006.01)
*G01N 33/68* (2006.01)

(52) U.S. Cl.
CPC . *G01N 33/54366* (2013.01); *G01N 33/54373* (2013.01); *G01N 33/6863* (2013.01);
(Continued)

(58) Field of Classification Search
CPC ....... G01N 33/54366; G01N 33/54373; G01N 33/6863; G01N 33/6866; G01N 33/6869
See application file for complete search history.

(56) References Cited

U.S. PATENT DOCUMENTS 4,661,444 A 4/1987 Li
5,296,719 A 3/1994 Hirai
(Continued)

OTHER PUBLICATIONS

Kim, Dong-Sun, et al. "An extended gate field effect transistor based protein sensor integrated with a Si micro-fluidic channel." Solid-State Sensors, Actuators and Microsystems, 2005. Digest of Technical Papers. TRANSDUCERS'05. The 13th International Conference on. vol. 2. IEEE, 2005.†

(Continued)

*Primary Examiner* — Melanie Yu Brown
(74) *Attorney, Agent, or Firm* — Pabst Patent Group LLP

(57) ABSTRACT

The present invention relates to a device and method for determining the presence of a specific compound in solution. The device includes a nanosensor having an electrically conducting pathway between at least a first and second contact. The device also includes a first receptor, suitable for binding a specific compound in the solution, attached to the nanosensor, and a second receptor also suitable for binding the specific compound while the specific compound is bound to the first receptor. The second receptor is attached to an enzyme added to the solution. When the solution having the second receptor is added to the device, and a second compound that is a substrate for the enzyme is subsequently added to the solution, a measured difference in an electrical property in the device before and after the application of the second compound is indicative of the presence of the specific compound in the solution.

10 Claims, 27 Drawing Sheets

Related U.S. Application Data continuation-in-part of application No. 12/517,230, filed as application No. PCT/US2007/024958 on Dec. 6, 2007, now Pat. No. 9,076,665.

(60) Provisional application No. 60/873,070, filed on Dec. 6, 2006, provisional application No. 60/873,740, filed on Dec. 8, 2006.

(52) U.S. Cl.
CPC ..... *G01N 33/6866* (2013.01); *G01N 33/6869* (2013.01); *G01N 2333/54* (2013.01); *G01N 2333/555* (2013.01); *G01N 2333/98* (2013.01)

(56) References Cited

U.S. PATENT DOCUMENTS

| | | | |
|---|---|---|---|
| 5,972,744 | A | 10/1999 | Morimoto |
| 6,069,380 | A | 5/2000 | Chou |
| 6,870,235 | B2 | 3/2005 | Abstreiter |
| 7,053,439 | B2 | 5/2006 | Kan |
| 7,893,466 | B2 | 2/2011 | Yang |
| 2002/0132273 | A1 | 9/2002 | Stryer |
| 2003/0124614 | A1 | 7/2003 | Utku |
| 2004/0119114 | A1 | 6/2004 | King |
| 2004/0121402 | A1 | 6/2004 | Harper |
| 2004/0136866 | A1 | 7/2004 | Pontis |
| 2004/0157268 | A1 | 8/2004 | Kobilka |
| 2005/0070802 | A1 | 3/2005 | Peters |
| 2005/0101841 | A9 | 5/2005 | Kaylor |
| 2005/0128788 | A1 | 6/2005 | Segal |
| 2005/0255491 | A1 | 11/2005 | Lee |
| 2005/0273867 | A1 | 12/2005 | Brulet |
| 2006/0003333 | A1 | 1/2006 | Puskas |
| 2006/0040378 | A1 | 2/2006 | Arinaga |
| 2006/0194263 | A1 | 8/2006 | Boussaad |
| 2007/0048180 | A1 | 3/2007 | Gabriel |
| 2007/0096164 | A1 | 5/2007 | Peters |
| 2007/0178477 | A1 | 8/2007 | Joiner |
| 2007/0196239 | A1 | 8/2007 | Vink |
| 2007/0231790 | A1 | 10/2007 | Su |
| 2007/0264623 | A1 | 11/2007 | Wang |
| 2007/0264634 | A1 | 11/2007 | Bock |
| 2008/0213956 | A1 | 9/2008 | Black |

OTHER PUBLICATIONS

Xuan, Guixin, et al. "Electrical effects of DNA molecules on silicon field effect transistor." International journal of high speed electronics and systems 14.03 (2004): 684-689.†

Pijanowska, Dorota G., and Wladyslaw Torbicz. "pH-ISFET based urea biosensor." Sensors and Actuators B: Chemical 44.1 (1997): 370-376.†

† cited by third party

NANOELECTRONIC-ENZYME LINKED IMMUNOSORBENT ASSAY SYSTEM AND METHOD

CROSS-REFERENCE TO RELATED APPLICATIONS

This application is a divisional of U.S. Ser. No. 12/535,396, filed Aug. 4, 2009, which is a continuation-in-part of U.S. patent application Ser. No. 12/517,230, filed Jun. 2, 2009, now issued U.S. Pat. No. 9,076,665, which is a National Stage Application of PCT International Application No. PCT/US07/024,958, filed Dec. 6, 2007, which in turn claims the benefit of U.S. Provisional Application No. 60/873,070 filed on Dec. 6, 2006 and U.S. Provisional Application No. 60/873,740, filed on Dec. 8, 2006, each of which is incorporated by reference herein in its entirety.

STATEMENT REGARDING FEDERALLY SPONSORED RESEARCH FOR DEVELOPMENT

This invention was made, in part, using funds obtained from the U.S. Government ARO, WF-11NF-08-1-0365 and NIH RO1 (EB008260). The U.S. Government also has a paid up license in this invention and the right in limited circumstances to require the patent owner to license others on reasonable terms as provided by the terms of Contract Nos. ONR K00134, AFOSR L00084, and AFOSR R06868 and graduate student fellowships that are supplied by the Department of Homeland Security and the National Science Foundation. The U.S. Government therefore has certain rights in the invention.

BACKGROUND OF THE INVENTION

There is an ever-increasing demand for miniature highly sensitive sensor devices suitable for manufacturing and industrial processing applications, environmental monitoring, as well as defense and homeland security applications. There is also a need for such devices capable of sensitive detection of biochemical and cellular responses in live cells and organisms. Indeed, the ability to rapidly detect minute concentrations of specific macromolecules is especially suited for clinical diagnostics, genomics, and drug discovery. However, conventional macromolecular sensing systems rely on labels, such as radiolabelled tags or fluorophores. There is currently a need in the art for devices, and methods, capable of label-free sensing. These devices, and methods, would likely significantly decrease the time needed for sample preparation, increase sample analysis throughput, and mitigate the need for target molecules modification.

One of the most promising platforms for label-free sensing is nano-wire field effect transistors (NW-FETs). These sensing devices, having the advantage of enhanced sensitivity due to the nano-scale channel confinement, operate by sensing the intrinsic charge of bound molecular species. For example, by binding a receptor protein or a single-stranded DNA (ssDNA) oligomer to the NW-FET surface, the binding of the specific ligand or complementary ssDNA modifies the electric field surrounding the device, enabling direct electronic detection.

Single-crystal, semiconducting NW-FETs are also attractive as biosensors due to their exquisite sensitivity to bound charge and potential portable format. Nanowire devices configured as solution-phase sensors or ion-sensitive FETs (ISFETs) have been demonstrated as ultrasensitive sensors. For example, solutions with physiologic salt concentrations have ionic (Debye) screening lengths of ~0.7 nm, which effectively neutralizes the molecular charge of a bound ligand beyond this distance. Thus, detection of such surface-bound ligands requires measurements to be performed in a low salt (1.5 mM) buffer to increase Debye screening lengths.

Although these, and other, silicon-based nano-sensors have been reported, they have exhibited poor sensing capabilities and their fabrication typically requires complex hybrid manufacturing methods having unreliable product performance and consistency. In addition, typical silicon-based nano-wire fabrication processes exhibit relatively poor material and device service life, thereby further discouraging nano-wire sensor incorporation into larger integrated detector systems.

Hence, there is a need for nano-sensor devices having improved sensing characteristics for enabling accurate and efficient detection of specific reagents in minute concentrations. There is also a need for a simplified fabrication process to produce nano-sensor devices having improved sensing capabilities that may be integrated into a variety of signal processing and information systems. Further, there is a need for a method that affects a solution pH change upon specific ligand binding.

SUMMARY

The present invention relates to a device for determining the presence of a specific compound in a solution. The device includes a semiconductor layer formed in or on a substrate; a channel having nano-scale cross-sectional dimensions formed in the semiconductor layer and forming an electrically conducting pathway between at least a first and second contact, wherein the channel includes at least one exposed lateral face; a first receptor, suitable for binding a specific compound in the solution, attached to at least a portion of the semiconductor layer or the at least one lateral face; a reservoir for holding the solution; and a second receptor that is suitable for binding the specific compound while the specific compound is bound to the first receptor, wherein the second receptor is attached to an enzyme and is added to the solution. When the solution having the second receptor is added to the device, and a second compound that is a substrate for the enzyme is subsequently added to the solution, a measured difference in an electrical property in the device before and after the application of the second compound is indicative of the presence of the specific compound in the solution.

In another embodiment, the enzyme is urease and the second compound is urea.

In another embodiment, the specific compound is a cytokine. In a further embodiment, the specific compound is an interleukin or an interferon.

In another embodiment, the first receptor is a monoclonal antibody.

In another embodiment, the reservoir is a microfluidic channel or a batch reservoir.

In another embodiment, the channel has at least one of a trapezoidal, square, round, ovoid and rectangular cross-section.

In another embodiment, the at least one first and second contact form at least one source and a drain contact, respectively, and a gate contact is applied on a top surface of the channel.

In another embodiment, the semiconductor layer is p-type.

In another embodiment, the semiconductor layer is n-type.

The present invention also relates to a method for determining the presence of a compound in a solution. In one embodiment, the method includes the steps of: i) attaching a first receptor, suitable for binding a specific compound in the solution, onto at least one exposed surface of a sensor, wherein the sensor includes a channel having nano-scale cross-sectional dimensions formed in a semiconductor layer and the channel has at least one exposed lateral face; ii) adding the solution to a reservoir of the sensor; iii) adding to the solution a second receptor that is suitable for binding the specific compound while the specific compound is bound to the first receptor, wherein the second receptor is attached to an enzyme; iv) adding to the solution a second compound that is a substrate for the enzyme; and v) measuring an electrical property in the sensor before and after the application of the second compound, wherein a difference in the electrical property is indicative of the presence of the specific compound in the solution.

In another embodiment, the determination of the presence of the specific compound in the solution is quantitative.

Further features and advantages of the present invention will be apparent from the following description of exemplary embodiments and from the claims.

BRIEF DESCRIPTION OF THE DRAWINGS

These and other features and advantages will be more fully understood by the following illustrative description with reference to the appended drawings, in which like elements are labeled with like reference designations, and in which the drawings may not be drawn to scale.

DETAILED DESCRIPTION OF THE INVENTION

The present invention provides a nanoelectronic-enzyme linked immunosorbent assay (ne-ELISA) for determining the presence and quantity of specific compounds in solution. The ne-ELISA is performed by a sensor that uses a nanowire to measure the concentration of the specific compound by sensing charge change in the vicinity of the nanowire. This is accomplished by monitoring the enzymatic conversion of a substance by an enzyme that is associated with the specific compound. In this way, the pH change due to enzyme activity functions as an indicator of the presence of the specific compound. Compound concentrations are also measured by comparing the measured rate of channel current decrease with the theoretical value derived from Michaelis-Menten enzyme kinetics, the Nernst potential, and the measured (dry) device transconductance.

Certain preferred embodiments of the present invention provide devices, and methods for their production, especially suited to sense a variety of molecular species, biological species, or cellular responses. In this manner, the species and/or substances of-interest may be detected and/or monitored. These species or substances can be present in solid, liquid or gaseous state in the ambient or can be applied to the device. Sensors of the present invention, for example, are especially suited for detecting, measuring, or both, of proteins, DNA and intrinsic cellular changes or cellular changes due to extrinsic stimuli. For example, the sensors may be particularly suited for detecting a specific ligand, such as interlukin-2 or any other cytokine. Still further, sensors, as described and provided herein, may also be suitable for sensing cellular interactions due to paracrine, autocrine, or endocrine signaling, or combinations thereof.

Sensors Types, Fabrication and Measurement

The detection device is implemented as an elongated nanostructure, for example, a nano-wire, and has an exposed surface that is substantially smooth and well defined. The nanostructure may be fabricated on a semiconductor substrate or on a semiconductor-on-insulator (SOI) substrate, wherein TMAH wet-etching is preferred. The exposed surface of the device used for detection may or may not be functionalized depending on the device's applications.

Figure 1:
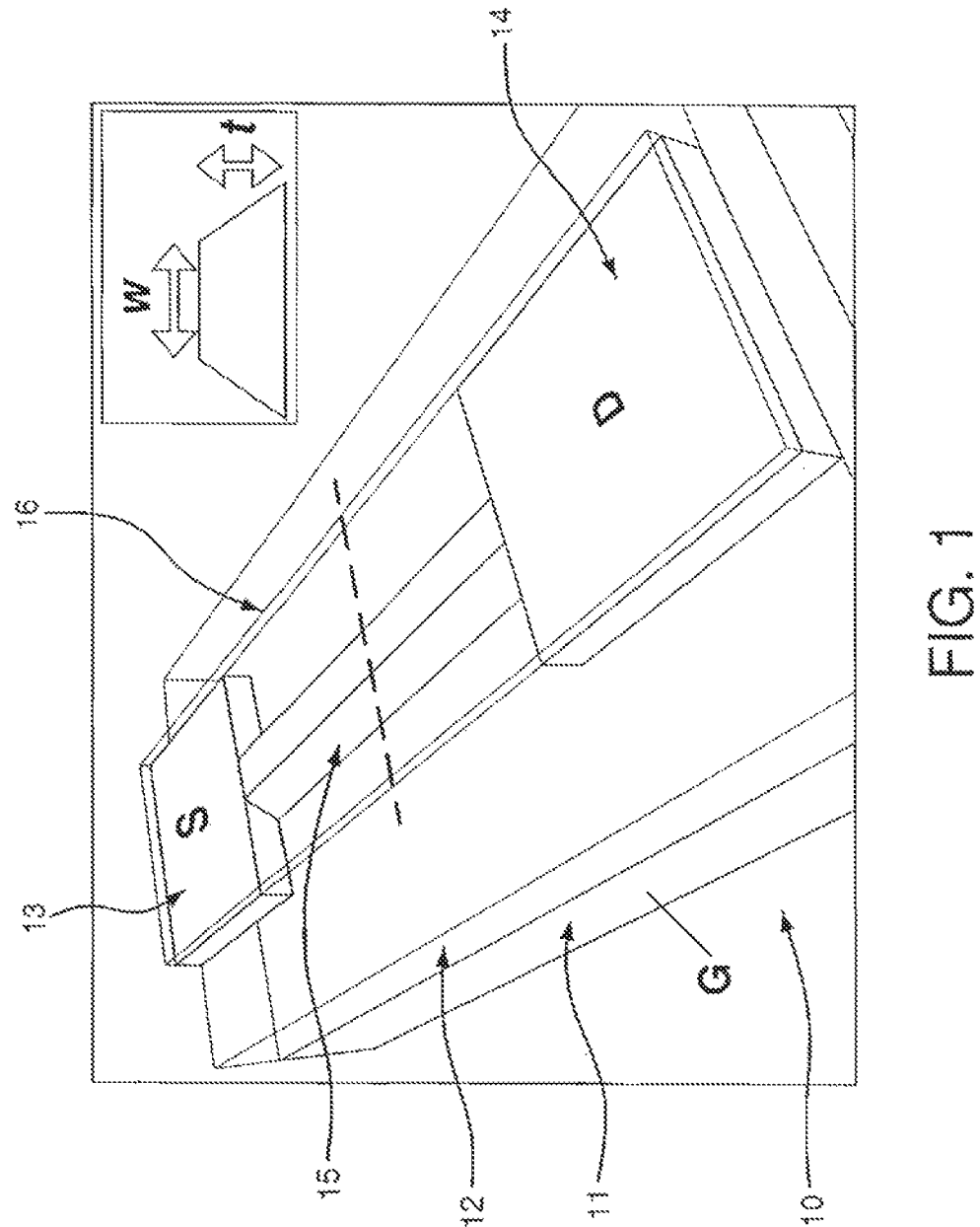
FIG. 1 is a schematic diagram of a nano-wire device, according to one embodiment of the invention, after anisotropic etching and before removal of the 600 nm wide masking oxide.

FIG. 1 shows a schematic diagram of a nanostructure sensor according to one embodiment of the invention. In this embodiment, the device is fabricated on a (100) silicon-on-insulator (SOI) wafer 10 which includes a silicon substrate 11, a thin $SiO_2$ layer 12 on the Si substrate 11 and a top Si layer on the $SiO_2$ layer 12, in which the source (S) contact 13, the drain (D) contact 14 and the actual nanostructure device 15, subsequently also referred to as nano-wire 15, are defined. Also shown is a $SiO_2$ layer 16 overlaying the contact 13, 14 and the device 15. The $SiO_2$ layer 16 in the illustrated example has a width of about 600 nm, from which the nano-wire device with a final width w (see inset) is then etched. The term "nano-wire" is not meant to imply that all lateral surfaces of the nano-wire are accessible from the outside. In the illustrated embodiment, the nano-wire 15 is prepared from the top Si layer and the bottom surface of the nano-wire 15 is therefore in direct material contact with the $SiO_2$ layer 12 and thus inaccessible.

The inset in FIG. 1 shows a cross-sectional view of the nano-wire 15 with a trapezoidal shape of thickness t and width w defined by the processing steps, which will be described in detail below. The sloped surfaces of the trapezoid represent the natural Si (111) planes, or cleavage planes, and may have an angle of about 54.7° between the (100) plane and the (111) plane.

Figure 2:
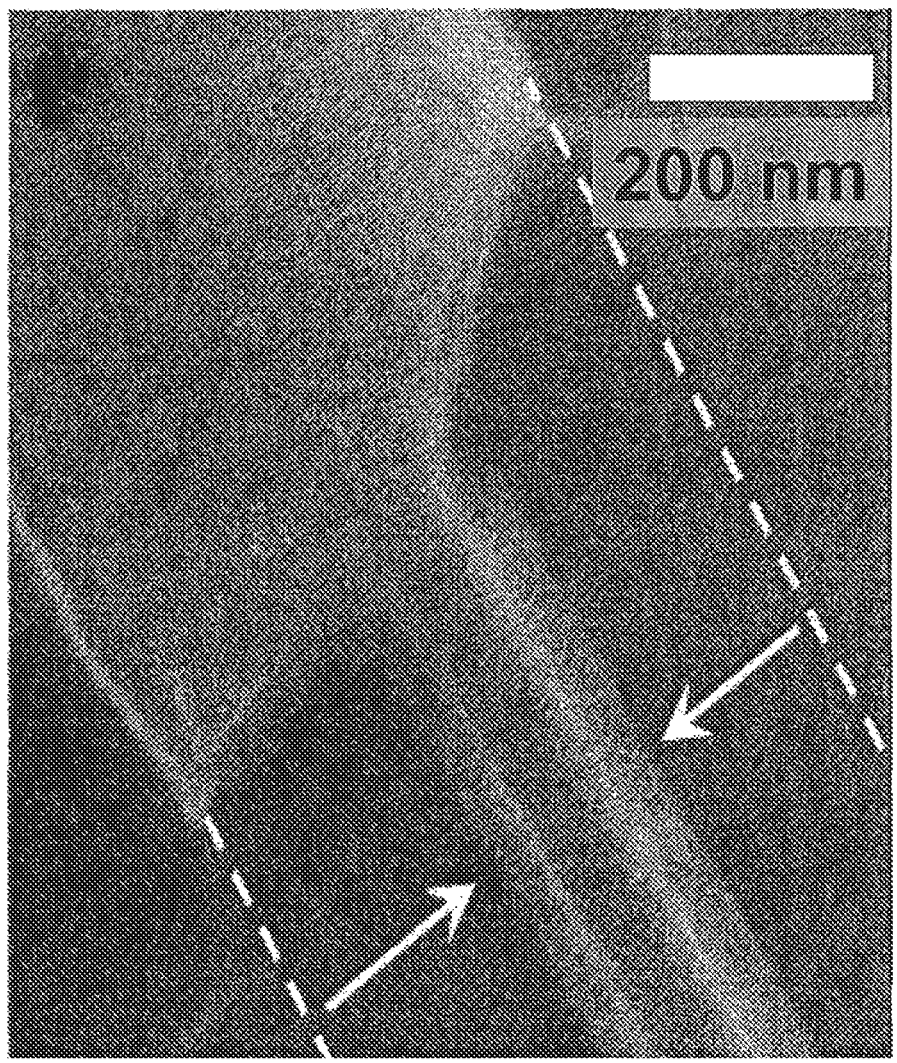
FIG. 2 is a scanning electron micrograph (SEM) of a completed device illustrating the x≈200 nm undercut etched from the sides of the masking oxide. The final device is 80 nm wide.

FIG. 2 is a scanning electron micrograph (SEM) of a detail near the source contact 13 of a finished device, where the top $SiO_2$ layer 16 has been removed. Although pattern-defined roughness is discernible near the contact regions, the sides of the device (i.e., the etched (111) silicon planes) appear substantially smooth without any visible surface roughness. Nano-wires with a controlled width of between about 50 nm and about 200 nm have been successfully prepared.

The width of the devices may be selected to optimize device sensitivity. As those skilled in the art will appreciate, the exemplary nano-wires form a conductive pathway between the contact regions 13 and 14 which, in the sensing operation, is affected by surface charges formed or deposited on or near the exposed lateral surfaces. These surface charges induce the greatest changes in the conductive pathway if they affect a substantial portion of the trapezoidal cross section of the device. The depth by which the surface charges extend from the exposed lateral surfaces inward is governed by the depletion width that in turn depends on the Debye length ($L_D$) of the semiconductor material from which the nano-wire is formed. The semiconductor characteristic Debye length may be presented as:

$$L_D \equiv \sqrt{\frac{\varepsilon_s kT}{q^2 N_B}} \quad (1)$$

wherein q is the electron or hole charge, $N_B$ is the doping density, T is the absolute temperature, and $\varepsilon_s$ is the dielectric constant of the semiconductor material. Exemplary values for $L_D$ at room temperature are $L_D \approx 100$ nm for $N_B = 10^{15}$ cm$^{-3}$, and $L_D \approx 10$ nm for $N_B = 10^{17}$ cm$^{-3}$. The values for $L_D$ of GaAs are identical to those of Si, whereas the values for Ge are greater by a factor of 1.16 due to the larger dielectric constant. The depletion width of the conduction nano-wire pathway, which depends on the Debye length ($L_D$) of the semiconductor material, can be changed by applying a gate voltage to a gate contact. The gate contact may be the silicon layer 11, operating as a back gate, or another contact layer disposed above the nano-wire 15, operating as a top gate (not shown).

In further detail, the charge of solution-based molecules and macromolecules is screened by dissolved solution counterions: a negative species such as streptavidin or DNA will be surrounded by positively charged ions due to electrostatic interactions. Accordingly, molecular charge screening by dissolved solution counterions—Debye screening—on sensor response can be evaluated. At a characteristic Debye length ($\lambda_D$), the number of net positive charges approaches the number of negative charges on the protein or DNA. The result is a screening effect such that the electrostatic potential arising from charges on the protein or DNA decays exponentially toward zero with distance. For aqueous solutions at room temperature, this Deybe length ($\lambda_D$) may be re-written from its previously described equation and now presented as $$\lambda_D = \frac{1}{\sqrt{4\pi l_B \sum_i \rho_i z_i^2}}, \quad (2)$$

where $l_B$ is the Bjerrum length=0.7 nm, $\Sigma_i$ is the sum over all ion species, and $\rho_i$ and $z_i$ are the density and valence, respectively, of ion species i. Thus, for optimized sensing, the Debye length must be carefully selected for NW-FET measurements since molecules binding to the devices are likely removed from the sensor surface by approximately 2-12 nm (the size of the receptor proteins or DNA linkers bound to the sensor surface). Debye length considerations, such as those now discussed, should likely be considered when designing preferred optimized protocols for label-free sensing, and such considerations may facilitate improved label-free sensing using NW-FETs. Indeed, proper consideration and optimization of Debye length selection ($\lambda_D$) may facilitate selective label-free sensing of macromolecules.

Figure 3A:
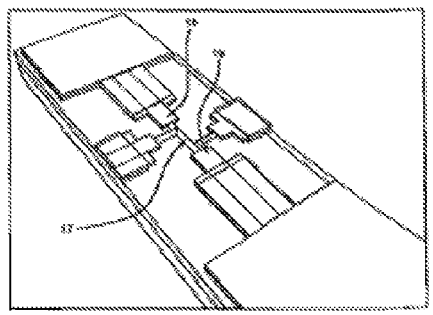
FIG. 3A is a schematic diagram (not to scale) of a four-point NW-FET device with source S, drain D, and gate G defined for a two-point sensing configuration. The TMAH-etched active sensing region 17 is shown.

In one preferred aspect of the present invention, nanowire-FET devices may be fabricated from silicon-on-insulator (SOI) wafers. For example, the NW-FET device regions may be defined with a wet chemical etch (tetramethylammonium hydroxide, TMAH), which etches Si (111) planes at approximately 1/100 the rate of all other planes and thereby eliminates edge imperfections not aligned to this plane. Electron-beam lithography and subsequent reactive-ion etching may be used to define the device dimensions in a thermally grown masking oxide, and TMAH etching to subsequently transfer the pattern to the active silicon layer. It should be noted that this etch produces trapezoidal devices due to the (100) orientation of the SOI wafers. As illustrated in the schematic in FIG. 3A, the etching causes undercutting of the masking oxide into the lightly-doped region (boron, $10^{15}$ cm$^{-3}$) 17, which in turn facilitates devices with significantly smaller dimensions than originally defined. The doped source contact 18 and drain contact 19 (each doped to >$10^{20}$ cm$^{-3}$ with boron by ion implantation) extend under the metal contact pads and are not appreciably etched by the TMAH. Four-point measurements showed that such devices exhibit negligible contact resistance such that sensing measurements can be made in a two-point configuration, as depicted in FIG. 3A.

Figure 3B:
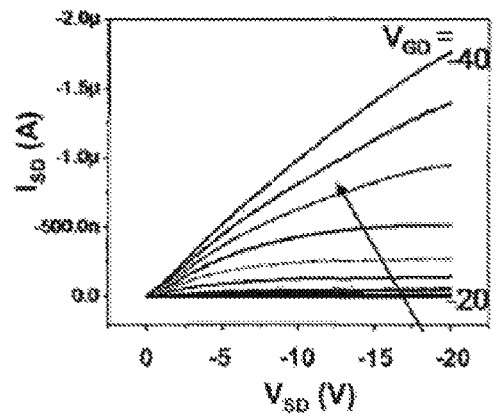
FIG. 3B is a graph depicting $I_{SD}$ ($V_{SD}$) dependence for $V_{GD}$ varied in –2V steps for a representative device in air before APTS functionalization.
Figure 3C:
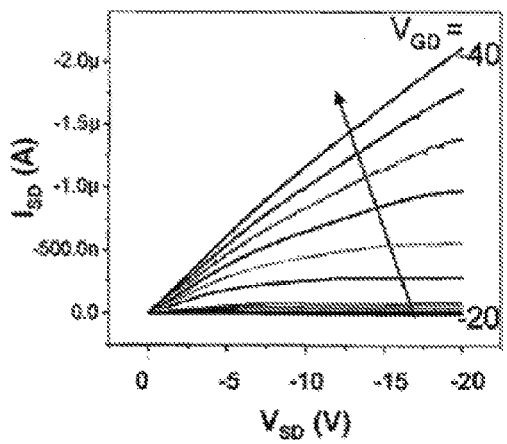
FIG. 3C is a graph depicting $I_{SD}$ ($V_{SD}$) dependence for $V_{GD}$ varied in –2V steps for a representative device in air after functionalization with APTS.

The transport characteristics of such device were measured before and after surface functionalization since surface chemistry interactions have been shown to have a deleterious effect on sensing properties. The dependence of source-drain current ($I_{SD}$) on source-drain voltage (VSD) for varying gate-drain voltage ($V_{GD}$) for a representative device is shown in FIG. 3B. In the instant case, sensing measurements used direct current having $V_{SD}$=−2V and $V_{GD}$=−35V. The large $V_{GD}$ required to turn on the device is consistent with SOI accumulation-mode operation. FIG. 3C shows that device functionalization with 3-aminopropyltriethoxysilane (APTS) to convert silanol (Si—OH) groups to free amines did not significantly affect the $I_{SD}$ (VSD) of the device. The relatively minute increase in $I_{SD}$ for large $V_{GD}$ suggests the presence of a small parallel current path through the surface. However, this path was not shown to appreciably alter the electronic characteristics when the device is fully depleted ($V_{GD}$≥−20V).

Figure 4:
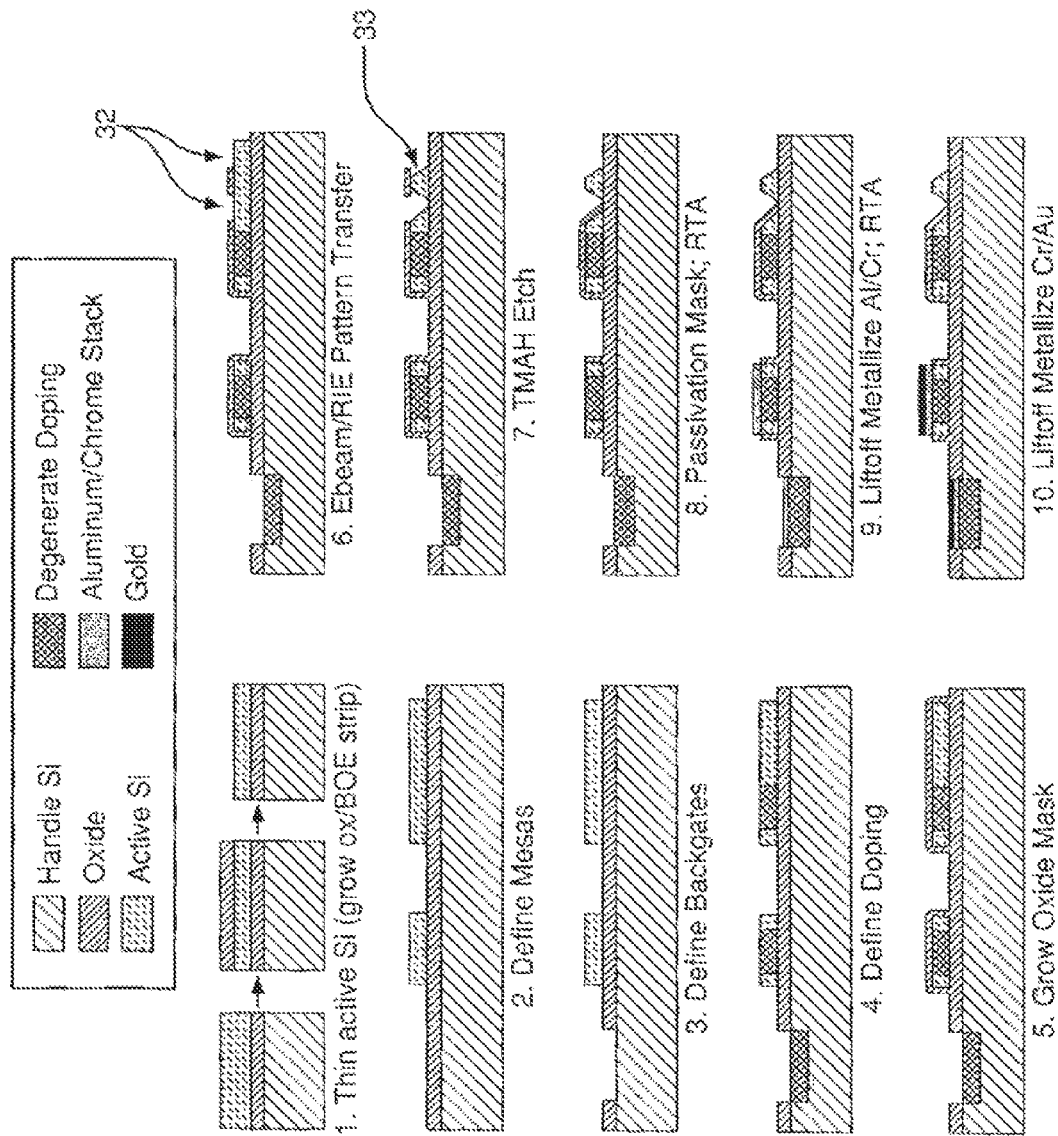
FIG. 4 is a diagram depicting the processing steps for fabricating the nano-wire sensor device according to the invention.

As mentioned above, the device structure, including the nano-wire 15, the contact regions 13, 14 and the contact to silicon layer 11, which may operate as a back gate, are fabricated on 4″ diameter SOI wafers 10. The active Si layers were thinned to about 25 nm, about 40 nm, and about 80 nm by oxidation followed by wet etching. An exemplary process for fabrication of the nano-wires according to one embodiment of the invention is depicted in FIG. 4. Step 1 shows the formation of an oxide by thermal oxidation of the top (active) Si layer of the wafer; the thermal oxide is then removed in a buffered oxide etch (BOE), leaving an active Si layer with a reduced thickness. In Step 2, those areas on the wafer 10 which will later define the source and drain contacts 13, 14 (as referenced by FIG. 1) and the region where the actual nano-wire 15 is formed, are delineated by contact lithography, and the top silicon layer outside the delineated areas is etched off by RIE to form mesas. Because the nano-wire is formed in a later process step (Step 7) by exposing the Si (111) surfaces, the silicon wafer is aligned at this point with the <110> wafer flat perpendicular to the orientation of the nano-wire. In Step 3, optical lithography and a two-step RIE are used to define a contact area for access to the back gate 11 (FIG. 1) and alignment marks in the handle wafer. In Step 4, the degenerate contact areas for the source contact 13 and the drain contact 14 are defined by optical lithography and formed by ion implantation. Arsenic ions are implanted for n-type conducting nano-wires (inversion-mode devices), and boron ions are implanted for p-type conducting nano-wires (accumulation-mode devices).

In Step 5, a thermal masking oxide (see layer 16 in FIG. 1) is grown over the implanted mesas and the gate contact area. In Step 6, the nano-wire pattern is transferred to the masking oxide by e-beam lithography and the masking oxide is removed in the unexposed areas, as indicated by the arrows 32. The areas outside the pattern shown in FIG. 1 with the reference symbol 16 are then etched down to the SiO$_2$ layer 12 by RIE, leaving the mesa defined by the area under the masking oxide 16 (see FIG. 1).

In Step 7, the wafer is etched in an anisotropic wet etch, in the present embodiment tetramethyl ammonium hydroxide (TMAH), which etches the Si (111) planes about 100 more slowly than other Si planes. Etching in TMAH retains the pattern defined by the masking oxide layer, but smoothes edge imperfections not aligned with the Si (111) plane.

Figure 5:
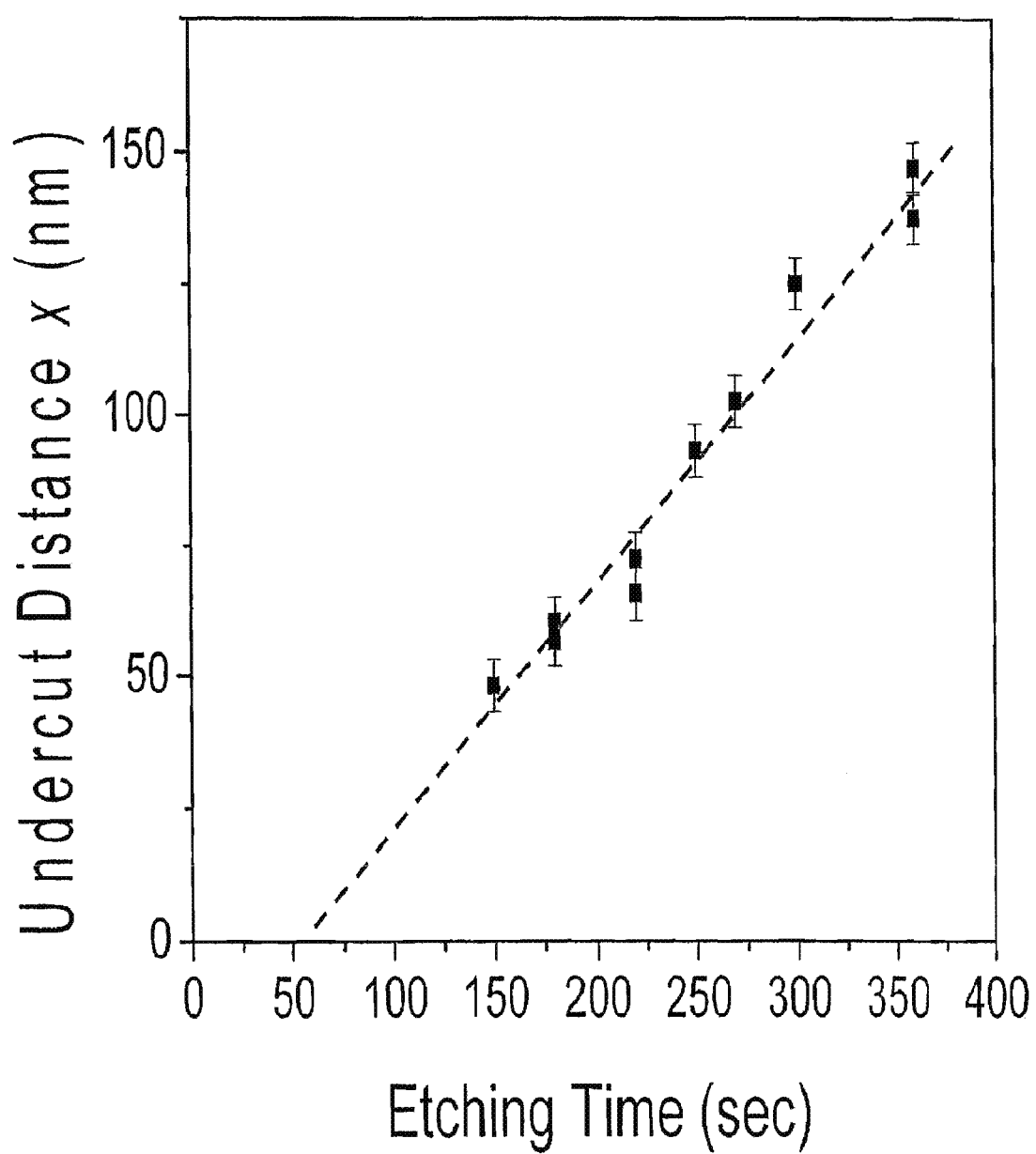
FIG. 5 is a graph demonstrating control of the lateral undercut distance as a function of the etching time for a TMAH etch.

FIG. 5 demonstrates the feature size control achieved with the TMAH etch. The undercut distance x (in nm) is plotted as a function of the etch time (in sec). The thickness of the active Si layer was t=80 nm and four devices are investigated. At each etch time, an average laterally TMAH-etched distance x is shown for four devices, with the error bars representing one standard deviation, indicating a feature size control of better than about 10 nm.

Returning now to FIG. 4, in Step 8, optical lithography and BOE are used to remove the masking oxide from the contact pads and the active nano-wire device, leaving the nano-wire exposed, as shown in FIG. 2. The samples are then annealed in forming gas in a Rapid Thermal Annealing (RTA) step. In Step 9, the contact area is delineated by optical lithography and metal contact pads are deposited on the source and drain contact pads 13, 14 and the gate contact area. The metal contacts pads are fabricated by conventional lift-off Aluminum (99.999%, Kurt J. Lesker Co.)/Chromium (99.998%, Kurt J. Lesker Co.) metallization followed in Step 10 by optical lithography and a Chromium/Gold metal stack deposited by lift-off. Those skilled in the art will appreciate that other metals compatible with silicon processing technology, in particular CMOS processing, may be employed.

Figure 6A:
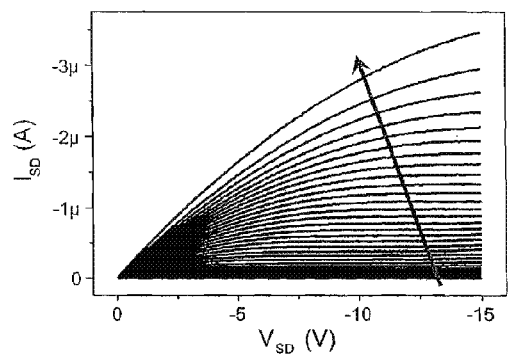
FIG. 6A is a graph depicting the electrical device characteristics of a p-type sensor.
Figure 6B:
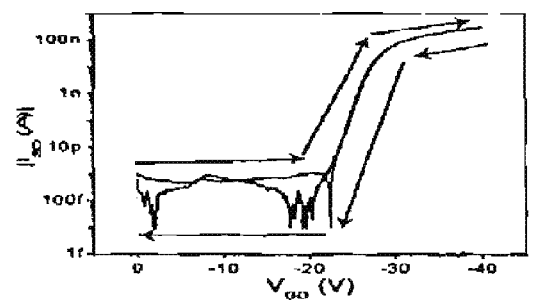
FIG. 6B is a graph of the source-drain current ($I_{SD}$) as a function of the gate-drain voltage ($V_{GD}$) for constant source-drain voltage for a forward and reverse sweep, indicated by the arrows, for the same p-type devices. The slope of this curve is commonly referred to as transconductance ($g_m$). The device hysteresis is seen to be minimal.

The afore-described fabrication process is flexible, allowing the configuration of a variety of sophisticated nano-wire geometries; for example, a 6-terminal Hall sensor, a 4-terminal device for accurate resistance characterization, and the described 2-terminal sensor. Sensor arrays and integrated signal processing electronics may be readily fabricated as well. FIG. 6A is a graph depicting the source-drain current ($I_{SD}$) as a function of the source-drain voltage ($V_{SD}$) of a p-type device (boron-doped silicon active layer) for various gate-drain voltages ($V_{GD}$) between 0 V to −40V in −1V steps (indicated by the bold arrow). The device has a width w≈50 nm, a thickness t≈25 nm and a length of 20 μm. The characteristics show p-type accumulation mode behavior. FIG. 6B shows for the same p-type devices the source-drain current ($I_{SD}$) as a function of the gate-drain voltage ($V_{GD}$) for constant source-drain voltage ($V_{SD}$) of=−1V for a forward and reverse sweep, indicated by the arrows. The slope of this curve is commonly referred to as transconductance ($g_m$). The device hysteresis is seen to be minimal.

Figure 6C:
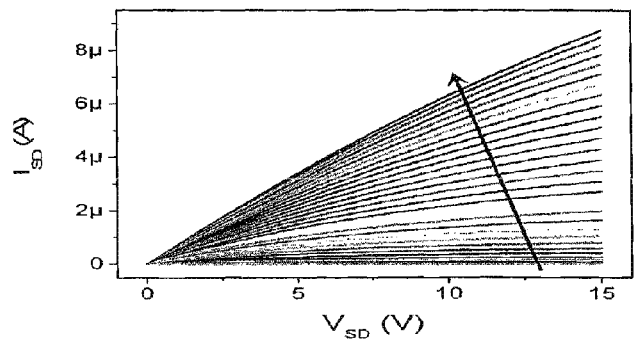
FIG. 6C is a graph depicting the electrical device characteristics of an n-type sensor.

FIG. 6C is a graph depicting the corresponding curves for n-type devices (arsenic-doped silicon active layer). The device has a width w≈50 nm, a thickness t≈40 nm and a length of 20 μm. The gate-drain voltage ($V_{GD}$) is varied between 0 V and +40V in steps of −+1V (indicated by the bold arrow). The characteristics show n-type inversion mode behavior. The almost imperceptible hysteresis between forward and reverse $I_{SD}$ ($V_{GD}$) in the region of maximum transconductance (steepest slope; see inset) suggest minimal defect-induced charge trapping.

In one embodiment, the Hall bar configuration of a silicon nano-wire makes it possible for the first time to measure the Hall mobility in the nano-wire, as shown in FIG. 6C. The peak drift mobilities may be calculated from the measured $I_{SD}(V_{GD})$ dependence and a self-consistent device simulation (Silvaco®). As depicted in FIG. 6C, an approximate average drift mobility of about 54 cm²/Vs is obtained, with a maximum value of 139 cm²/Vs. The device had a width w≈2300 nm, and a thickness t≈25 nm. These results compare favorably with mobility data for bulk p-type silicon doped to $10^{15}$ cm$^{-3}$, which has a bulk mobility of 450 cm²/Vs. Hole mobilities are typically smaller than electron mobilities by about a factor of 2. The bulk mobility is known to decrease for anisotropically defined Si (111) planes.

This described device fabrication process provides inherent back-gating capability of the nano-wire channel, which permits the sensitivity of a device to be tuned through operation in different transconductance ($g_m$) regions, which is important for applications requiring a high dynamic range. Transconductance is a measure of the dependence of the source-drain current $I_{SD}$ on the gate voltage $V_{GD}$ and may be presented as:

$$g_m = \left(\frac{\partial I_{SD}}{\partial V_{GD}}\right)_{V_{SD}=const} \quad (3)$$

The sensor response to changes in the surface charge will occur at the maximum transconductance value ($g_{m,max}$). This maximum value is reached between the linear region and the saturation region of an FET transfer characteristic.

The useful gate voltage $V_{GD}$ for optimized device performance depends on the actual device parameters, for example, the electric field induced by the gate in the conductive channel of the nano-wire, i.e., the thickness of the SiO$_2$ layer 12 (FIG. 1). In the described exemplary embodiments, this SiO$_2$ layer 12 is quite thick, typically about 100 nm, so that large gate voltages $V_{GD}$ are required. A decrease of the gate voltage can be expected with a thinner SiO$_2$ layer 12.

As disclosed elsewhere herein, both boron-doped p-type devices and arsenic-doped n-type devices can be prepared. Fabrication of these complementary devices is compatible with conventional silicon CMOS processing. The nano-wire sensor devices can therefore become part of an integrated system with on-chip signal processing, error detection, and complementary detection to avoid false positives. Complementary devices are useful for detecting, for example, small concentrations of antibodies, which will be described in detail below.

The active region of the nano-wire devices may be between about 1 μm to about 100 μm long, with a thickness between about 25 nm to about 100 nm. A width at the top of the trapezoidal cross-section may be etched down to about 10 nm. In general, the thinner the active region of the nano-wire, the larger its surface area-to-volume ratio.

Although the illustrated nano-wire devices in the exemplary embodiments are fabricated on an SOI wafer with the underlying silicon substrate operating as a back gate, a gate electrode can also be applied on top of the nano-wire. Alternatively, the top silicon active layer can be insulated from the substrate by a reverse biased p-n junction. In an alternative embodiment, the nano-wires may be formed in compound semiconductors, such as GaAs, GaAlAs, GaAlInAsP and other III-V compound semiconductors, or in any other materials that exhibit a low intrinsic surface state density that can be altered by an externally applied surface charge. As compound semiconductor layers with different composition respond differently to chemical etchants, the fabrication of devices in compound semiconductor materials may include the formation of etch stop layers which may be used to define the narrow dimensions of nano-wires.

Figure 7:
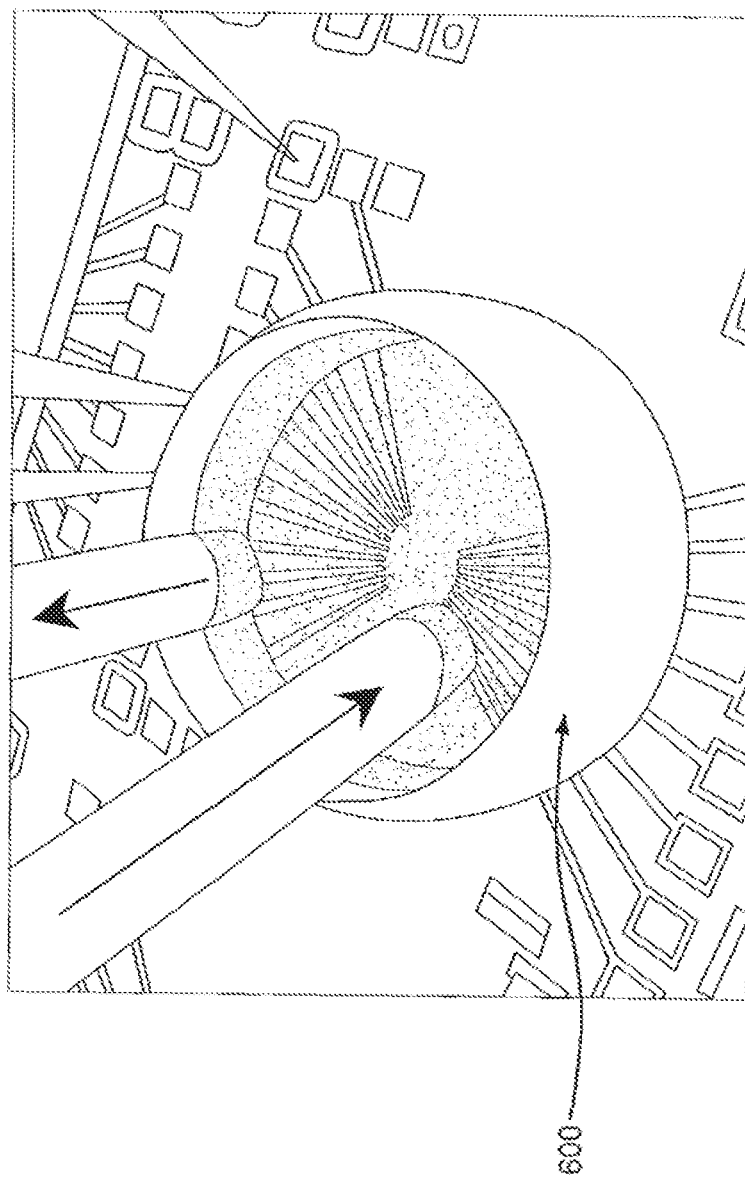
FIG. 7 is a diagram illustrating a solution chamber according to one embodiment of the invention.

In certain embodiments, a macro-scale solution chamber 600 is provided to facilitate the characterization of liquid-phase sensor response by the nano-wire device. FIG. 7 illustrates an exemplary solution chamber 600 configured to induce mixing of fluids that are continuously supplied to the nano-wire structure for solution-based electrical response measurement. These fluids may be specific media that are conducive to cellular growth or homeostasis. In a preferred configuration, this solution chamber 600 is designed to avoid the well-characterized limits on sensitivity and response time inherent in diffusion-limited systems, such as in microchannels.

According to one aspect of the invention, the nano-wire structure of FIG. 1 acts as a sensor for monitoring ionic changes of various substances. More specifically, substances of varying ion compositions, when introduced onto the native oxide surface of the nano-wire device, are adapted to alter the nano-wire's surface potential and effectively gating the underlying device. Hence, the nano-wire structure provides a sensitive and measurable means by which ionic changes of various substances may be accurately monitored in real-time. For example, given a p-type nano-wire device, if the pH of a solution introduced to the surface of the nano-sensor is lower than pH of the device's native oxide coating, then the absorption of the solution onto the oxide coating results in the protonation of the oxide surface, thus depleting the hole-carriers in the device, resulting in an increase in its surface charge density, and causing a decrease in its source-drain conductivity. Conversely, when a solution having a higher pH level is introduced to the p-type nano-sensor, the sensor's oxide surface is adapted to deprotonate, causing a subsequent decrease in its surface charge density and an increase in its conductivity. In addition, n-type nano-wires are equally operable as miniaturized sensors for the screening of real-time molecular responses. N-type nano-wire structures will be described below in greater detail. In certain implementations, the unfunctionalized nano-sensors show enhanced device sensitivity towards interaction-dependent conductivity responses when the device surface area is reduced. In certain implementations, the nano-sensors display favorable characteristics such as small hystereses and high reproducibility, where the average detected current levels are repeatable to less than about 15% error.

Figure 8A:
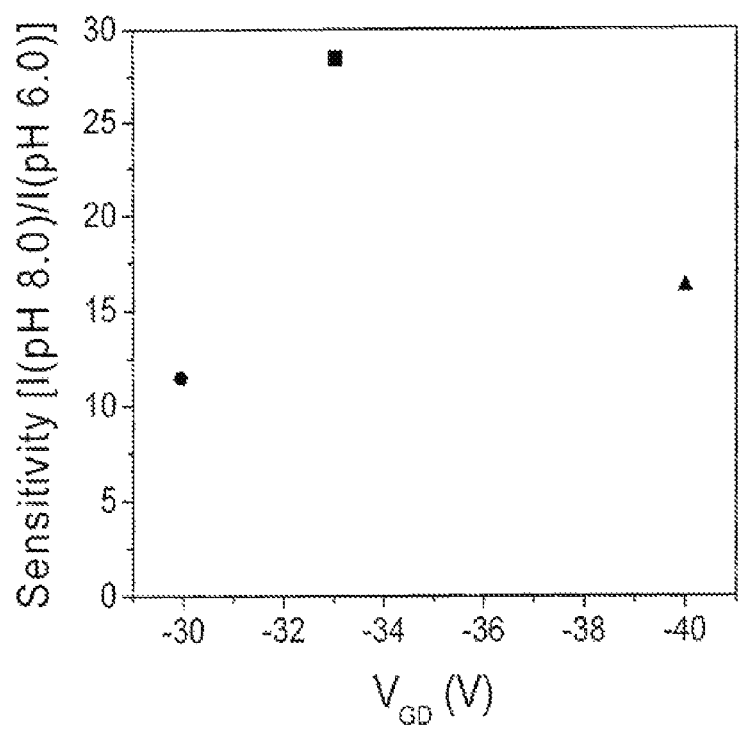
FIG. 8A is a graph illustrating sensitivity and transconductance responses, both as functions of gate-drain voltage, in an unfunctionalized p-type nano-wire sensor.
Figure 8B:
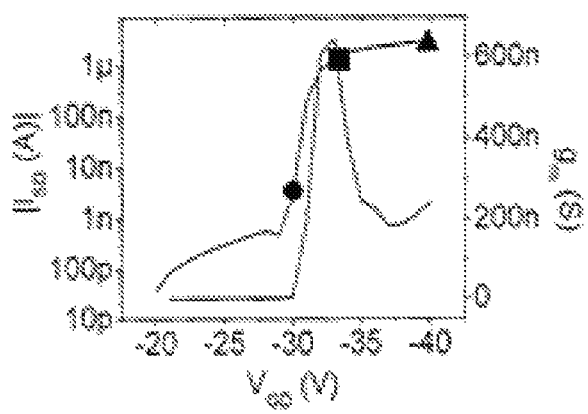
FIG. 8B provides an exemplary plot of a sensor's source-drain current ISD, and transconductance gm dependencies on gate-drain voltage VGD at a constant source-drain voltage VSD of –1V.

In one embodiment, the unfunctionalized nano-sensors of the present invention is implemented into an architecture containing a back-gate for tuning the sensitivity of the device to operate within a specific transconductance ($g_m$) region. In general, transconductance is a measure of current response with respect to gate voltage. Thus, transconductance measurements provide a quantifiable approach for a user to tune the sensitivity of the nano-sensor to sense specific substances whose detection is desirable to the user. FIG. 8B provides an exemplary plot of a sensor's source-drain current $I_{SD}$, and transconductance $g_m$ dependencies on gate-drain voltage $V_{GD}$ at a constant source-drain voltage VSD of −1V. With reference to FIG. 1, the sensor has a cross-sectional thickness of about 40 nm and a cross-sectional width of about 150 nm, where this cross-sectional width refers to the smaller of the trapezoidal widths characterizing the device's cross section. FIG. 8 also illustrates a plot of the sensor's sensitivity ratio as a function of $V_{GD}$. As depicted, the sensor's measured sensitivity tracks with its measured transconductance over the range of $V_{GD}$ values. In particular, FIG. 8 shows that the most sensitive sensor response to additional surface charge occurs at the maximum transconductance state $g_{m,max}$, which is between the linear and saturation regions of the device's transfer characteristic. Hence, the sensitivity of a nano-sensor may be optimized by applying appropriate voltages to the back-gate such that the sensor device is operating at $g_{m,max}$. Due to the dynamic range of sensitivities provided by gating, a nano-sensor may also be tuned to a sensitivity level as specified by a user. For example, the back-gate is used to tune chemical potential of the nano-sensor to a particular reaction such that only the signal from that reaction is electronically recognized by the sensor. Furthermore, a dynamic feedback loop may be coupled to the tunable nano-sensor device to perform automatic and optimized sensitivity correction. In addition, one or more top-gates, lateral-gates, side-gates or any combination thereof are used to tune the nano-sensor to operate within a specific transconductance, and hence sensitivity, state.

Figure 9:
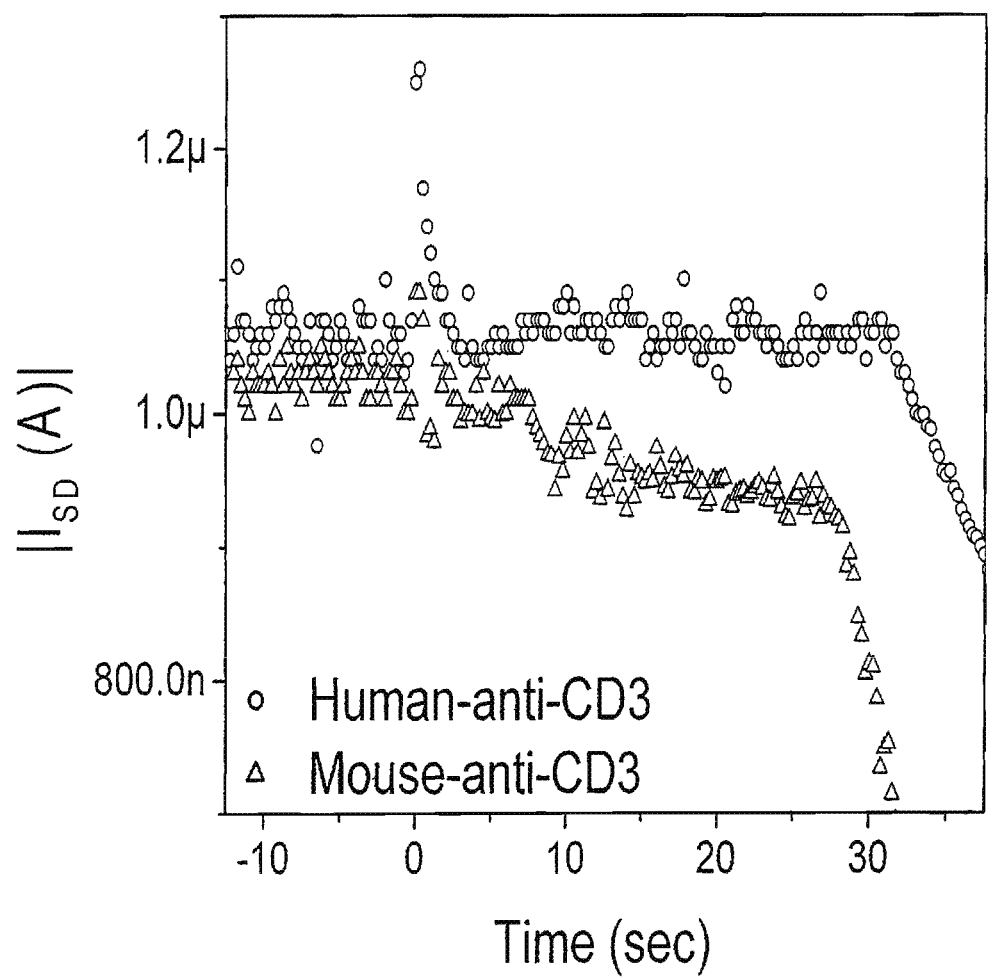
FIG. 9 is a graph illustrating conduction current responses in biotin-functionalized p-type nano-wire sensors to the addition of human-α-3 and mouse-α-3 stimulants.

As described above, unfunctionalized nano-wire devices may act as ion sensors for sensing pH and other ionic changes of substances disposed on its native oxide surface. In one embodiment, such unfunctionalized nano-wire devices are used to monitor real-time cellular responses of activation-induced changes in extracellular pH. For example, real-time T-lymphocyte activation may be monitored using a nano-wire sensor, where the T-cell activation may be triggered by antibody-mediated crosslinking of cell-surface CD3, which induces intracellular signaling and, subsequently, engages effector mechanisms. One consequence of such activation includes the release of acid that alters the surface charge density of the sensor. In one illustrative implementation, a species-specific antibody directed against mouse CD3 complex (mouse-α-3) is added to a suspension of mouse splenocytes containing about 6000 mouse-derived T-cells. This solution is then introduced to a nano-sensor, having a cross-sectional width of about 100 nm and a cross-sectional thickness of about 40 nm, to detect T-cell activation by the mouse-α-3 stimulant. As illustrated in FIG. 9, the subsequent decrease in extracellular pH caused by the T-cell activation corresponds to an approximate 7.3% decrease in average current measured by the nano-sensor after a current baseline is established for about 10 seconds. This current continues to decrease until current instability occurs after about 30 seconds of sensing.

In another illustrative implementation, an antibody specific to human CD3 (human-α-3-CD3) complex, which does not bind to mouse CD3, is added to the same suspension of mouse splenocytes as described above. Hence no mouse-derived T-cell activation is expected to take place. This is confirmed by electrical current measurements taken from the sensor device, as shown in FIG. 9, which indicates that minimal change in current has resulted from the addition of the human-α-3-CD3 stimulant.

Figure 10A:
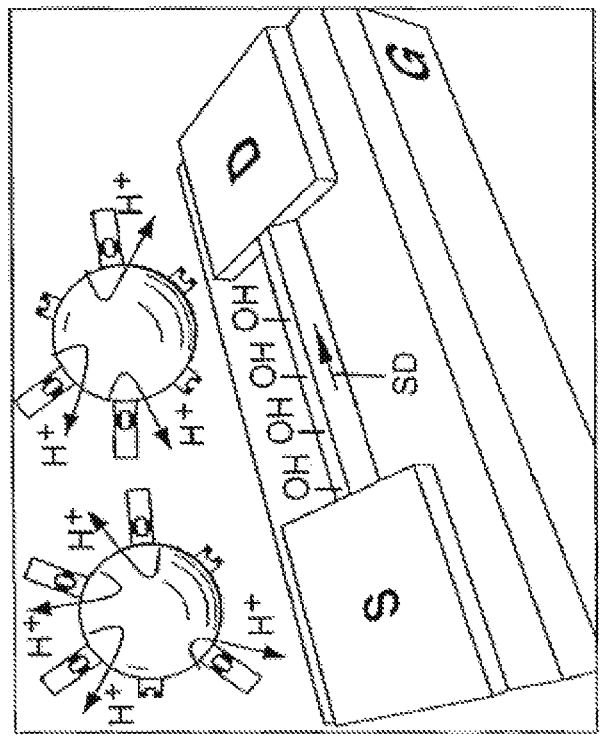
FIG. 10A is a diagram of a sensing schematic prior to T cell stimulation. Prior to T cell activation, a majority of the nanowire's silanol groups (active region colored black) are deprotonated.
Figure 10B:
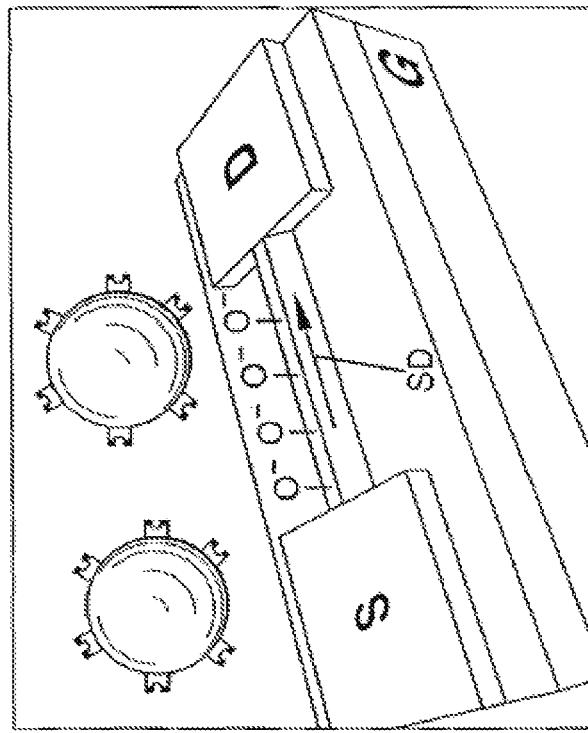
FIG. 10B is a diagram of a sensing schematic post T-cell stimulation. After stimulation+activation, extracellular acidification results in increased protonation of the surface silanol groups, which decreases $I_{SD}$.

Yet other illustrative embodiments may be useful for sensing certain aspects of proton secretion due to activation-induced polyclonal T-cell signaling. FIGS. 10A and 10B shows a sensing schematic: pre-T cell stimulation and post-stimulation+activation, respectively. Prior to T cell activation, a majority of the nanowire 20 silanol groups are deprotonated. After activation, extracellular acidification results in increased protonation of the surface silanol groups, which would decrease $I_{SD}$. The time required for T cell activation after stimulant addition can be quantified.

Figure 11A:
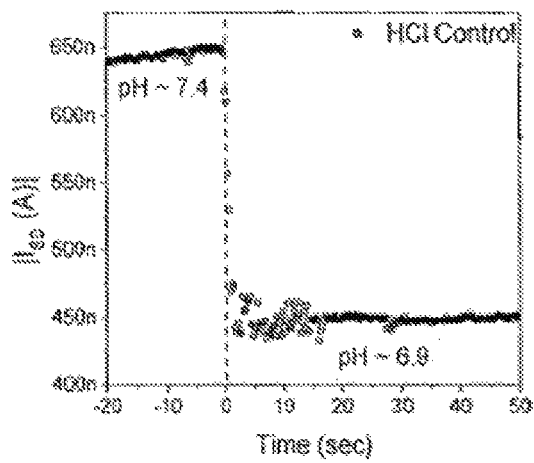
FIG. 11A is a graph depicting device response up to 50 seconds to the addition of 1 mL of dilute hydrochloric acid to a cell-free buffer, demonstrating system response of approximately 1.5 sec.; Solution pH values are also provided.
Figure 11B:
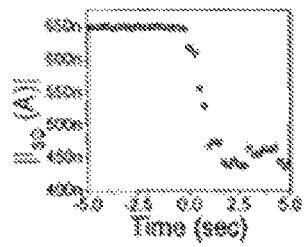
FIG. 11B is a graph depicting device response up to 5 seconds to the addition of 1 mL of dilute hydrochloric acid to a cell-free buffer, demonstrating system response of approximately 1.5 sec.
Figure 11C:
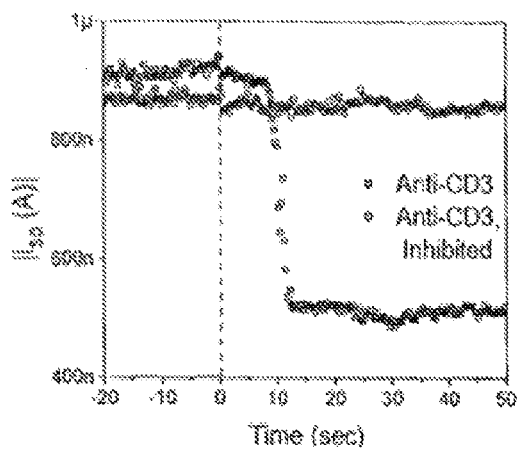
FIG. 11C is a graph depicting measurement of extracellular acidification upon stimulation of B6 splenocytes with anti-CD3. The T cell response time is approximately 8 sec. Pre-treatment of splenocytes with genistein (50 mg/mL), which inhibits cell signaling, eliminates anti-CD3 induced cellular metabolic activity.

For example, splenocytes isolated from a C57BL/6 (B6) mouse were suspended in a low-buffered solution and stimulated with anti-CD3 antibody. FIG. 11C shows that extracellular acidification was observed to begin approximately 8 sec after injection. Without being limited by theory, approximately 8 sec delay observed in FIG. 11C was believed to be primarily due to intrinsic cellular processes. To ensure that extracellular pH changes were due to stimulation-induced cellular metabolic activity, splenocytes derived from the same mouse were treated with genistein, an antibiotic that inhibits the induced intracellular signaling cascade, without affecting cellular viability. FIG. 11A shows that the presence of genistein, addition of anti-CD3 antibody resulted in no change in solution pH. This confirmed that the positive response observed in untreated cells was due to anti-CD3 antibody-initiated proton secretion from splenocytes.

Figure 12A:
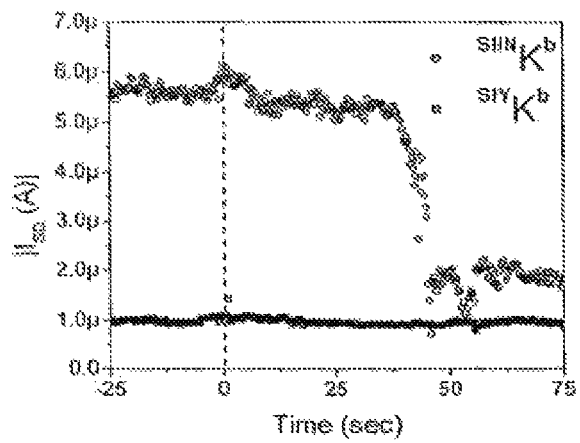
FIG. 12A is a graph depicting OT-1 stimulated with $^{SIIN}K^b$ and $^{SIY}K^b$ dimeric constructs. Extracellular acidification began at approximately 40 sec for the positively-stimulated splenocyte population.
Figure 12B:
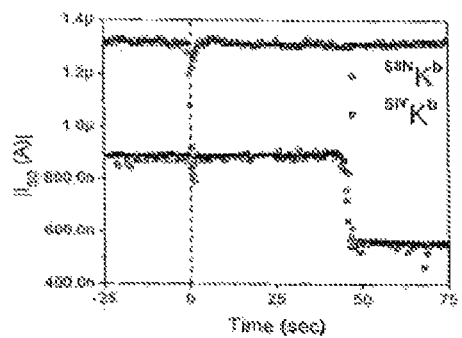
FIG. 12B is a graph depicting 2C splenocytes stimulated with $^{SIIN}K^b$ and $^{SIY}K^b$ dimeric constructs extracellular acidification began at approximately 40 sec. for positively-stimulated splenocyte population.

Still other embodiments were are suitable for discriminating between well-established peptide-specific MHC restricted responses of T-cell clones. For example, murine splenocytes isolated from 2C and OT-1 transgenic mice were stimulated with dimeric MHC ligands presenting their cognate and non-cognate peptides. 2C and OT-1 CD8$^+$ T-cells (cytotoxic T-lymphocytes, CTLs) react against a broad range of defined peptides presented by syngeneic MHC Class I, H-2K$^b$. OT-1 mice, expressing a transgene for the T-cell antigen receptor, are reactive with the complex of H-2K$^b$ and the ovalbumin octapeptide SIINFEKL ($^{SIIN}K^b$). As a negative control for this system, the inventors used a non-cognate peptide derived from a peptide library, SIYRYYGL ($^{SIY}K^b$). Cytotoxic T-lymphocytes from 2C transgenic mice should be reactive to $^{SIY}K^b$ but exhibit a null response to $^{SIIN}K^b$). Using a NW-FET sensor of the present invention, a drop in solution pH beginning approximately 40 sec after addition of $^{SIIN}K^b$ dimer to OT-1 splenocytes was observed; no response was observed after addition of $^{SIY}K^b$ (FIG. 12A). Conversely, 2C CTLs reacted to the presence of the $^{SIY}K^b$, with proton secretion beginning approximately 40 sec after peptide/MHC addition. The device showed no discernable changes in conductance when $^{SIIN}K^b$ was added to 2C splenocytes (FIG. 12B).

The observed onset of extracellular acidification of T-cells upon stimulation with peptide/MHC, after a lag of approximately 40 sec, was longer than that measured for anti-CD3 antibody stimulation, the approximately 8 sec. There were believed two candidate mechanisms potentially responsible for the observed delay: 1) the kinetics of T-cell activation are strongly affected by the dwell time of the T-cell receptor-activating stimulus. Antibodies that trigger the CD3 complex bind with higher affinities ($K_d$ approximately 1-10 nM) than peptide/MHC complexes ($K_d$ approximately 1-100 µM), which may lead to faster intracellular signaling, resulting in earlier acid release. 2) A smaller population of responsive cells (typically approximately 20-30% of all transgenic splenocytes are reactive to the specific antigen) may require a longer time for accumulation of the signaling molecules needed to achieve sufficient extracellular acidification.

Figure 12C:
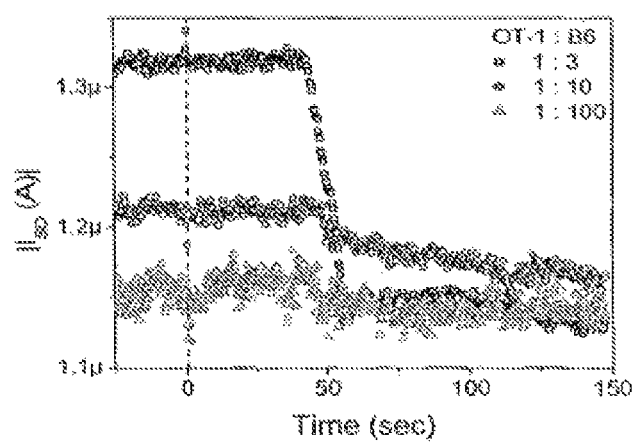
FIG. 12C is a graph depicting OT-1 splenocytes diluted to various ratios with wild-type B6 splenocytes; CTL. The response to stimulation with $^{SIIN}K^b$ was measured.

Stimulating dilutions of OT-1 cells mixed with background splenocytes derived from B6 mice was used to distinguished between these possible mechanisms. Upon stimulation with cognate antigen ($^{SIIN}K^b$), FIG. 12C shows a decrease in device signal intensity with decreasing numbers of OT-1 cells. The observed responses were produced by OT-1 splenocyte populations of approximately 28000, 7000, and 700 cells for the 1:3, 1:10, and 1:100 dilutions, respectively. The onset of stimulus-induced extracellular acidification began approximately 45-49 sec for all dilutions, indicating that the strength of the stimulus, rather than changes in the cell density, was responsible for the delay. These data are consistent with previous studies that monitored the dynamics of intracellular calcium flux (which had similar response times) after stimulation with different agonists and showed that the apparent lag time after antigen-specific T-cell triggering correlated with signal strength.

These, and still other, exemplary embodiments illustrate that the nano-sensors of the present invention are suitable for the accurate and efficient monitoring of real-time cellular responses based on sensing activation-induced changes without tagging or labeling the pertinent reagents involved in the reactions. The enhanced device sensitivity also contributes to the efficiency with which detections are enabled. Indeed, such illustrative nano-sensor are suitable for label-free detection of stimulus-induced extracellular acidification within seconds after stimulation of a small number of cells, <210 (30% of 700). Illustrative NW-FET sensor sensitivity, rapid response time, low required sample volume, and suitability for high-throughput analysis show great applicability towards a variety of clinical and diagnostic applications.

Nano-sensors of the present invention, and their associated methods of use, may be used in diagnostic applications that require the accurate discrimination among cells primed against different pathogens. For example, HIV infected cells (lymphocytes) respond to HIV antigens via activation-induced changes in T-cell functions. Thus, lymphocytes isolated from healthy and diseased donors who are non-responsive and responsive, respectively, to HIV antigens can be easily and quickly screened in a label-free manner using the sensor device of the present invention.

Unfunctionalized nano-sensors may also be used to monitor other real-time cellular responses based on the sensing of activation-induced extracellular ionic changes. For example, the nano-sensor devices may be used to detect the stimulation of T-cells, neutorphil, basophil, dendritic, macrophage, regulatory and natural killers, and other cells of the immune system. In these applications, stimuli of the respective cells are used to discriminate among the cells primed against specific antigens. Each interaction is likely to trigger extracellular changes in ions that are detectable by the sensor device due to a correlated change of the device conduction current. Exemplary ionic changes include changes related to hydrogen ions, calcium ions, ATP ions, and other ions that tend to propagate during cellular responses. Exemplary stimuli include antibodies, peptide or major histocompatibility complexes, carbohydrates, nucleotides, synthetic polymers and monomers, and other ligands that tend to trigger cellular functions.

In yet another application, unfunctionalized nano-sensor devices may be used to ascertain protein and macromolecule stability and aggregation potential because as these molecules unfold, for example, upon exposure to a denaturant, the molecules tend to change the electrical properties of the nano-sensor whereon the molecules are applied. The resulting change in device conduction current can be used to deduce a stability measurement for each molecule, hence providing a facilitated approach to assess the propensity of the molecule towards aggregation which potentially leads to one or more diseased states. For example, detection of unfolding and aggregation of amyloid peptides may be a warning sign for Alzheimer's. Detection of crystalline peptide aggregation may be a warning sign for cataracts.

In another application, the nano-wire sensors may be used to detect exocytosis, which is essential to normal cell functions and forms the basis of intercellular communication in multi-cellular organisms. Exocytosis involves the intracellular and intercellular transport of membrane-bound vesicles that tend to release their content upon fusion with other cells. Hence, the sensor device of the present invention may be used to detect exocytosis by sensing changes in the device's electrical properties in correlation to degranulation, or the release of substances, from the vesicles. Secreted substances include proteins, carbohydrates, ions, nucleotides or other macromolecules with a net surface charge that impacts the charge of the sensor. More specifically, the sensor device is able to detect pathological cells in connection to two known types of exocytosis. Constitutive exocytosis occurs independent of extracellular stimuli. Often, this type of exocytosis is dysfunctional in diseased or infected cells. Therefore, the ability to monitor constitutive exocytosis is important to differentiating between normal and pathological cells without the presence of a stimulus. Regulated exocytosis occurs when cells are triggered by a stimulus which may lead to secretion of hormones, acidic granules, second messengers, digestive enzymes and other molecules. Again, dysfunction in regulated exocytosis may be indicative of pathology. Often, pathological cells secrete granules in response to external stimuli such as the way HIV-infected cells respond to HIV antigens or autoimmune cells respond to autoimmune antigens. The sensor device is able to measure exocytic secretion of granules resulted from both constitutive and regulated exocytosis. In addition, the sensor device is able to distinguish between cells capable and incapable of secreting granules. In certain exemplary applications, exocytosis in neurons, endocrine neurons, neuroendocrine/endocrine cells, exocrine cells and hemopoietic cells are detected by the sensor devices based on their secreted granules which tend to alter the electrical properties of the devices. These secreted granules include, for example, dense-core vesicles, chromaffin granules, secretory granules, mucin granules, lamellar body, zymogen granules, casein vesicles, lysosome-related granules and other molecules.

In yet another application area, the nano-wire device of the invention is able to distinguish between apoptotic and non-apoptotic cells, which is critical to discriminating between pathological and non-pathological states in many types of cancer as well as to the detection of autoimmune and alloimmune disease states. In general, dying cells that undergo the final stages of apoptosis rearrange the cell surface and certain phospholipids on the cell surface. For example, phosphatidylserine that are normally found on cytosolic (inner) surface of a plasma membrane are redistributed during apoptosis to the membrane's extracellular surface. Because cell membranes are typically negatively charged, apoptosis results in a reduction of the overall charge which impacts device electrical properties upon the introduction of the cells onto the device surface. In many cases, this reduction of charge is in addition to an overall degranulation and secretion of cytoplasmic factors that take place during the apoptostic process.

Functionalization of Sensor Surfaces

According to another aspect of the invention, in addition to using unfunctionalized sensor devices to monitor real-time cellular responses, the detection capability of the nano-sensor may be expanded via selective sensor surface functionalization which permits sensing of desired ions in addition to protons as well as sensing of disparate indicators for a variety of cellular assays. For example, a nano-sensor may be functionalized by receptor molecules that bind to specific reagents, in which case a conductance change occurs in the corresponding sensor device. Given a p-type nano-wire, its conductance is adapted to increase when a macromolecule with negative surface charge binds to a nano-wire surface functionalized with receptor molecules, whereas the opposite response occurs when a positively-charged molecular binding occurs on a functionalized device surface. Hence functionalized nano-wires are well suited for performing selective label-free sensing of macromolecules. In addition to p-type nano-wire functionalization, selective n-type nano-wire functionalization is equally viable for performing label-free sensing. Details regarding n-type nano-wire sensors will be described below.

Some functionalization methods, such as hydroxyl-reactive schemes, require the functionalization of the entire sensor surface, including the underlying oxide, which diminishes sensitivity of the nano-sensor due to binding competition. Thus, selective device functionalization is critical to the retention of sensitivity. A selective device functionalization process is provided according to an embodiment of the present invention, according to which nano-wires are introduced into an inert $N_2$ atmosphere, etched for about 5 seconds in 10:1 buffered oxide etch, rinsed and dried, coated with a functionalizing solution, and subjected to about a 2 hour UV treatment. Deprotection may be performed with 25% TFA in methylene chloride utilizing any prior art procedure. After washing and deprotecting, the yield of the device for effective selective functionalization is less than about 2%.

Dec-9-enyl carbamic acid tert-butyl ester may be used to functionalize nano-sensor devices because this substance has been shown to confer amine functionality. Dec-9-enyl carbamic acid tert-butyl ester may be synthesized using any prior art procedure. This molecule is the same as 10-N-boc-amino-dec-1-ene, which has been shown to selectively functionalize silicon-over-oxide. All chemicals required for synthesizing dec-9-enyl carbamic acid tert-butyl ester may be purchased from Sigma-Aldrich. H NMR (500 MHz, $CDCl_3$) $\Delta$5.79 (1H, ddt, J=17, 10.2, 6.7 Hz, CH), 4.98 (1H, dd, J=17, 1.7 Hz, CH), 4.91 (1H, dd, J=10.2, 1.7 Hz, CH), 4.88 (1H, s, NH), 3.09 (2H, m, $CH_2$), 2.03 (2H, m, $CH_2$), 1.47-1.29 (12H, m, $CH_2$), 1.44 (9H, s, $CH_3$); $^{13}C$ NMR (500 MHz, $CDCl_3$) $\Delta$156.06, 138.98, 114.20, 78.68, 40.62, 33.80, 30.12, 29.43, 29.29, 29.06, 28.92, 28.46, 26.83.

Figure 13:
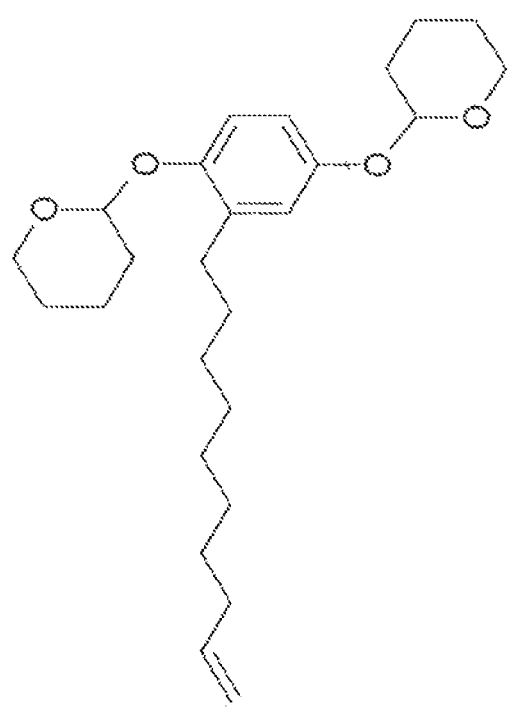
FIG. 13 is a structure of an exemplary 2-[4-(tetrahydro-2H-pyran-2-yloxy)phenoxy]tetrahydro-2H-pyran molecule.

Another functionalization substance may be 2-[2-(undec-10-enyl)-4-(tetrahydro-2H-pyran-2-yloxy)phenoxy]tetrahydro-H-pyran. This molecule, whose structure is shown in FIG. 13, may be synthesized from 2-[4-(tetrahydro-2H-pyran-2-yloxy)phenoxy]tetrahydro-2H-pyran using any prior art process. The intermediate may be synthesized by first adding dihydropyran (0.83 mL, 9.1 mmol) and pyridinium p-toluenesulfonate (0.11 g, 0.45 mmol) to a solution of hydroquinone (0.25 g, 2.3 mmol) in $CH_2Cl_2$ (3 mL) This reaction mixture is then stirred for about 12 hours and diluted with 10 mL of $CH_2Cl_2$. The mixture is subsequently washed by 3×5 mL of $NaHCO_3$ and 1×5 mL brine, dried over $MgSO_4$, and concentrated to a white solid. Silica gel chromatography (4:1 hexane/ethyl acetate) provides the di-tetrahydropyran hydroquinone as a white solid (0.48 mg, 75%).

Figure 14A:
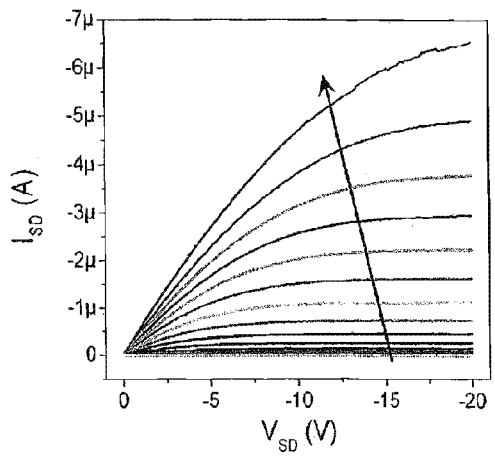
FIG. 14A is a graph depicting source-drain current ($I_{SD}$) versus source-drain voltage ($V_{SD}$) for various gate-drain voltages ($V_{GD}$) applied to an unfunctionalized p-type nano-wire sensor and a p-type nano-wire sensor functionalized with dec-9-enyl carbamic acid tert-butyl ester.
Figure 14B:
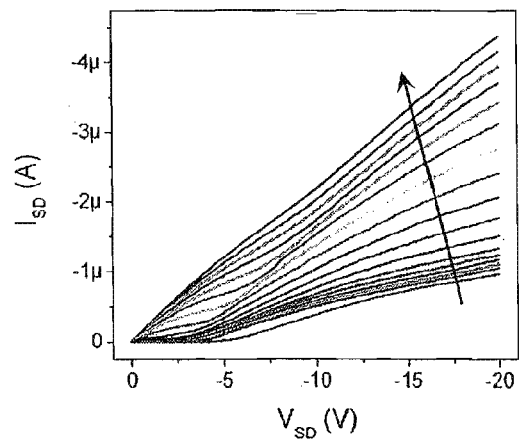
FIG. 14B is a graph depicting source-drain current ($I_{SD}$) versus source-drain voltage ($V_{SD}$) for various gate-drain voltages ($V_{GD}$) applied to an unfunctionalized p-type nanowire sensor and a p-type nano-wire sensor functionalized with dec-9-enyl carbamic acid tert-butyl ester.
Figure 14C:
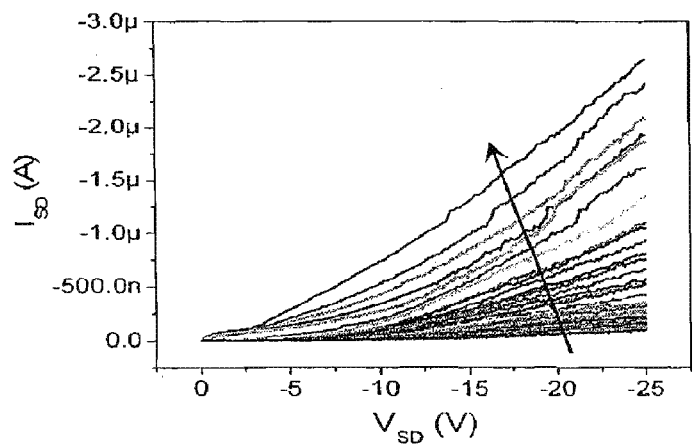
FIG. 14C is a graph depicting $I_{SD}$ versus $V_{SD}$ for various $V_{GD}$ applied to a p-type nano-wire sensor functionalized with 1-decene.

In certain embodiments, optimal device operation regions are determined for nano-sensors selectively functionalized with each of the aforementioned substances. After device functionalization and deprotection with dec-9-enyl-carbamic acid tert-butyl ester, as shown in FIGS. 14A and 14B, respectively, absence of device pinch-off is observed for source-drain voltages $V_{SD}$ that are less than about −5V ($-V_{SD}$>5V), hence suggesting a possible occurrence of parallel conduction at high bias through the functionalization layer which induces the creation of alternative conduction paths. However, at $V_{SD}$ greater than about −5V ($-V_{SD}$<5V), the current leakage is negligible and the device is well suited for sensing. Thus, for certain functionalized nano-sensor operations, the $V_{SD}$ is maintained at −2V or above for optimal sensing. Similar device operation regions may be applied to devices functionalized with 1-decene, whose conductivity response is shown in FIG. 14C. In certain implementations, dec-9-enyl-carbamic acid tert-butyl ester and 1-decene are preferred as functionalization substances over 2-[2-(undec-10-enyl)-4-(tetrahydro-2H-pyran-2-yloxy)phenoxy]tetrahydro-H-pyran because the latter substance may destroy the gating behavior of some nano-wire devices.

Figure 15A:
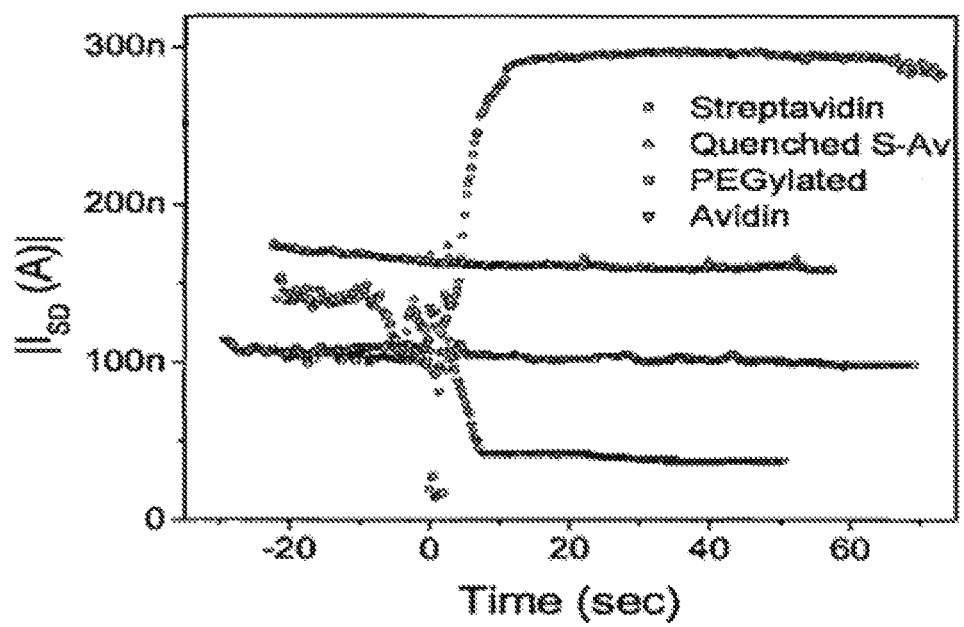
FIG. 15A is a graph illustrating conduction current responses in biotin-functionalized p-type nano-wire sensors to the addition of streptavidin, quenched streptavidin, and avidin. Current response is also shown for a poly(ethylene glycol) (PEG) functionalized sensor device to the addition of streptavidin.

Functionalized nano-sensors may be used to detect certain macromolecules based on selective protein binding. According to one example, electrical responses of biotin-functionalized device to the addition of 1 nM streptavidin, 1 nM biotin-quenched streptavidin, which is streptavidin pre-treated with 5 equivalents of biotin, and 1 nM avidin are determined. In order to avoid the problem of Debye screening, the salt concentrations in the buffers used for macromolecular sensing are chosen such that the Debye screening length ($\lambda_D$) is long enough not to impede sensing, but short enough that unbound macromolecules are screened. As shown in FIG. 15A, addition of a streptavidin solution results in a current increase in the nano-sensor due to the protein's negative charge, hence demonstrating selective protein recognition and the dependence of device electrical signal on protein charge. However, addition of biotin-quenched streptavidin to a biontin-functionalized nano-wire sensor elicits no response as demonstrated by the minimal fluctuation observed in the measured current shown in FIG. 15A. However, device current noticeably drops upon introduction of avidin, having an isolectric point (pI) of about 0.5, due to avidin's positive charge. In additional examples of selective functionalization, a poly(ethylene glycol) (PEG) functionalized device yields no conduction response to an addition of 1 nM streptavidin (pI about 5.6), which is also illustrated in FIG. 15A.

Figure 15B:
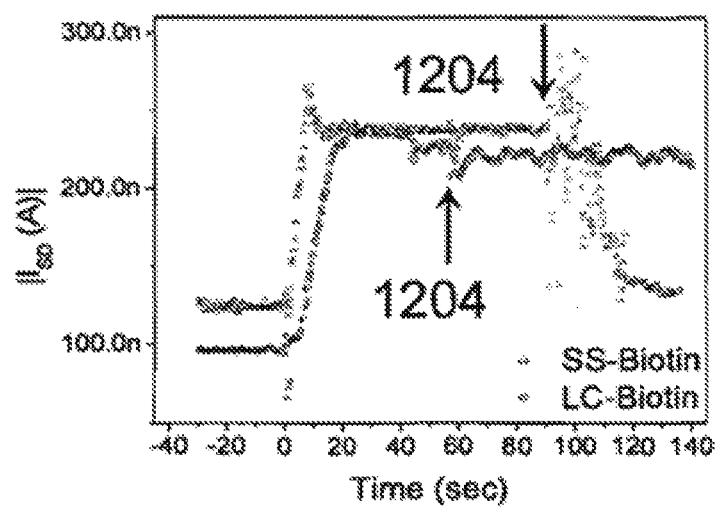
FIG. 15B is a graph demonstrating the reversibility of p-type nano-wire sensor response to streptavidin addition and removal.

According to another embodiment, functionalized nano-sensors are capable of reversing sensor responses to the addition or removal of reagents. In one exemplary implementation, the reversibility of sensor response to streptavidin addition and removal is demonstrated. Biotinylation, or biotin functionalization, of a single sensor is performed with a cleavable molecule SS-biotin, which may be processed from sulfo-NHS-biotin with a 2.4-nm linker having a dithiol bond. A second sensor is biotinylated with a noncleaving molecule LC-biotin that may be processed from sulfo-NHS-biotin with a 2.2-nm PEG linker. The response of each sensor to 1 nM streptavidin addition is similar, as illustrated in FIG. 15B. Subsequently, a reducing agent, tris(2-carboxyethyl)phosphine (TCEP), is added to the nano-sensor, as shown by the arrow 1204 of FIG. 15B. The addition of the reducing agent cleaves the disulfide bond between the SS-biotin and the streptavidin which subsequently reverses the sensor response to baseline current. However, the LC-biotin control, which does not cleave disulfide bonds, is insensitive to the reducing agent and produced minimal response.

Molecular charge screening by dissolved solution counterions—Debye screening—on sensor response may evaluated. Certain embodiments of the present invention were functionalized with APTS to effect amine-modified surfaces in high yield (>90%). Conventional shortcomings of the APTS technique—that essentially the entire NW-FET would be functionalized with amines—are thought to dramatically decrease sensing device sensitivity. Accordingly, certain preferred functionalized embodiments of the present invention were pattered to provide a final photoresist layer that exposed only a small region around the active devices as depicted by FIG. 3A.

Figure 16:
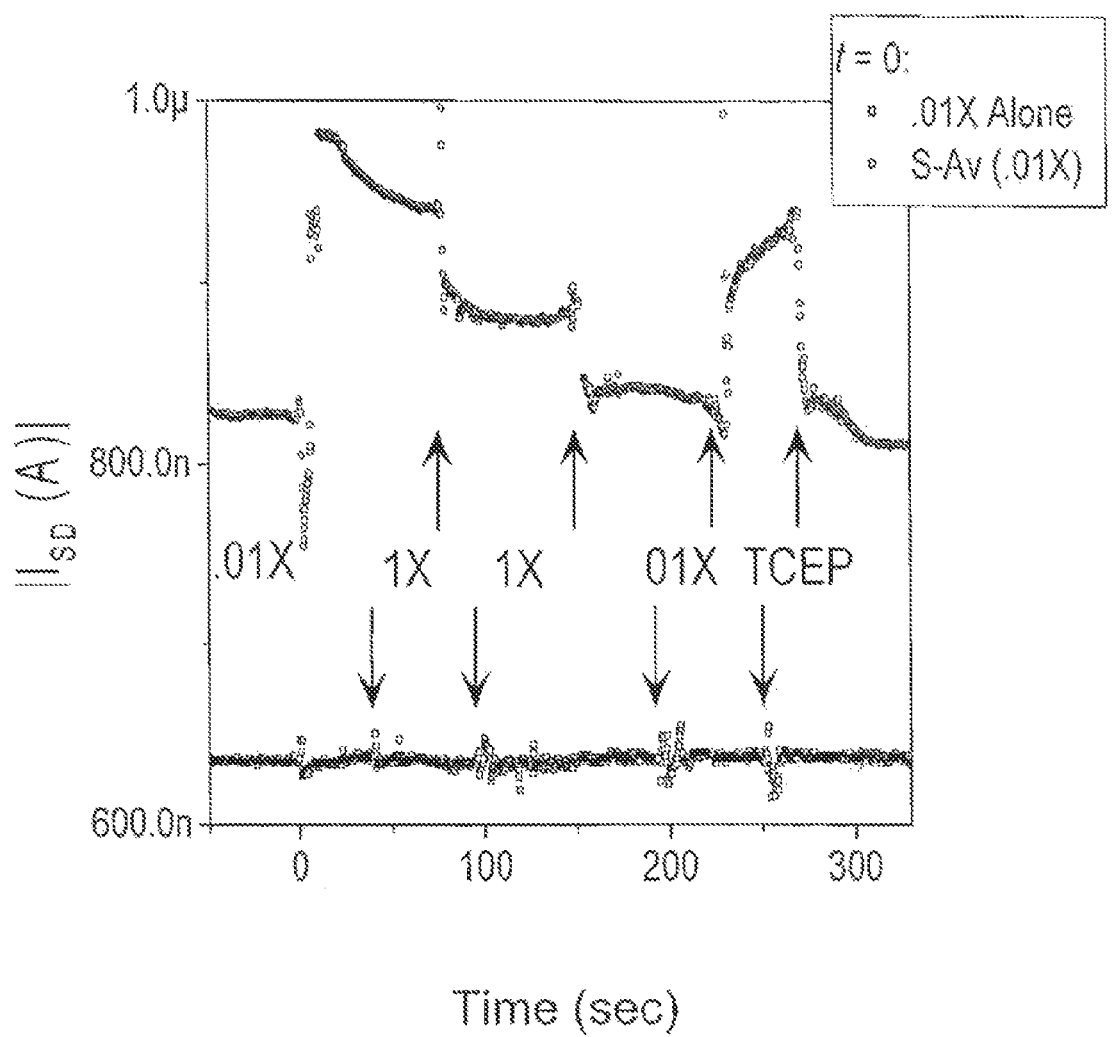
FIG. 16 is a graph demonstrating biotin-functionalized sensor response ($|I_{SD}|$ vs. time) to varying buffer ionic concentrations with, and without, streptavidin addition at time=0.

Next, the effect of increasing buffer ionic strengths (decreasing Debye length—$\lambda_D$) on device recognition sensitivity was determined. A NW-FET device, of the present invention, was functionalized with a cleavable biotin molecule and, after establishing a baseline current in 0.01×PBS, 10 nM streptavidin was added in the same buffer. The binding of streptavidin, a negative protein with an isoelectric point (pI) of approximately 5.6, to the biotinylated device resulted in an increased $I_{SD}$ of the p-type device (FIG. 2B). The ionic strength of this buffer yields a $\lambda D$ of approximately 7.3 nm. Thus the majority of the protein's charge is unscreened at the NW-FET surface (FIG. 16B). A ten-fold increase in the ionic strength of the buffer (0.1×PBS, $\lambda D$ approximately 2.3 nm) partially screens streptavidin's intrinsic charge and a further ten-fold increase in buffer ionic strength (1×PBS, $\lambda_D$ approximately 0.7 nm) effectively screens most of the protein's charge, returning the $I_{SD}$ approximately to its baseline value (FIG. 16B). The device current level begins to recover to its 0.01×PBS value after a subsequent decrease in ionic strength by solution exchange with this buffer. The addition of the reducing agent tris(2-carboxyethyl)phosphine hydrochloride (TCEP), which cleaves the biotin linker and, thus, removes streptavidin from the sensor surface, returns $|I_{SD}|$ to its original baseline level, see FIG. 16B. As a control, the same series of solution exchanges was applied to a nominally identical biotinylated device using streptavidin-free buffers (FIG. 16B). The absence of a change in signal demonstrates that the NW-FET response is independent of ionic strength (e.g., $\lambda_D$).

Figure 17A:
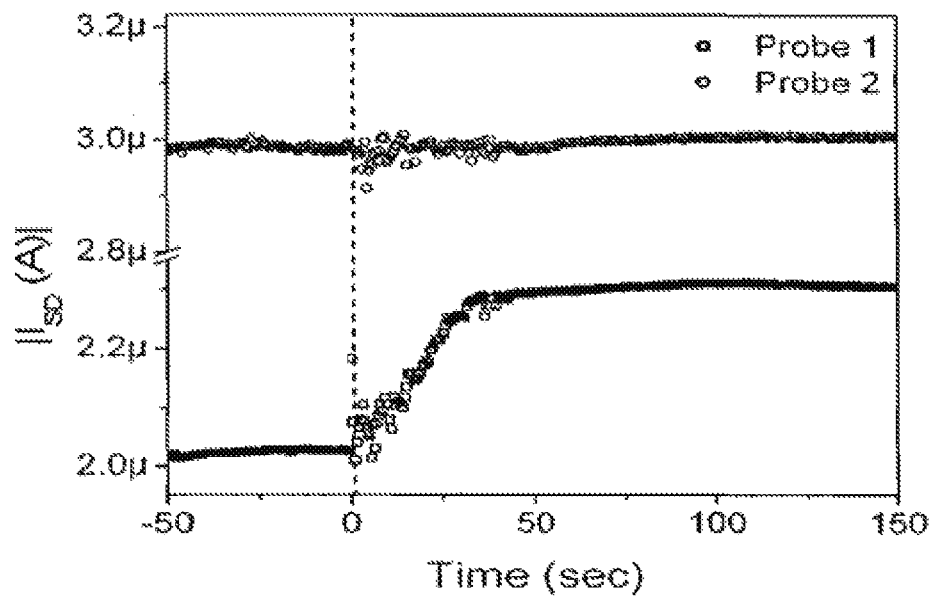
FIG. 17A is a graph demonstrating the response of NW-FETs functionalized with the Probe 1 DNA strands to the addition of 10 pM solutions of target DNA strands. Solution exchange occurs at time=0, highlighted by the dashed line.
Figure 17B:
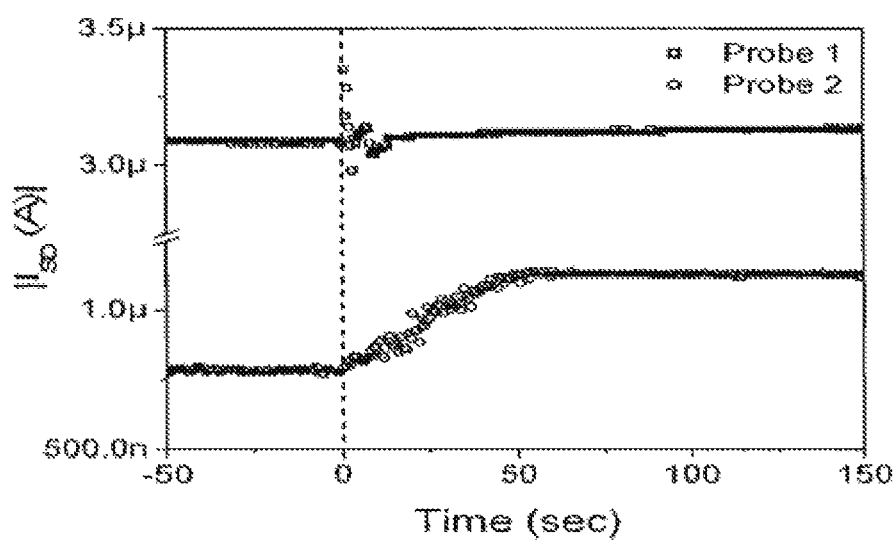
FIG. 17B is a graph demonstrating the response of NW-FETs functionalized with the Probe 2 DNA strands to the addition of 10 pM solutions of target DNA strands. Solution exchange occurs at time=0, highlighted by the dashed line.

For yet other certain preferred embodiments, cross-comparison assays were performed to determine device suitability for specific ssDNA strand recognition. For example, two exemplary NW-FET devices were functionalized with the DNA-P(1) sequence and two devices with the DNA-P(2) sequence. All such devices having a Debye length ($\lambda_D$) of about 3.3 nm relative to the NW-FET sensor surface. Under active measurement conditions ($V_{SD}$=−2V, $V_{GD}$=−35V) and after the establishment of a baseline signal in 0.05×PBS, the solution was exchanged with 10 μM solutions of target DNA, either DNA-T(1) or DNA-T(2), in the same buffer. FIGS. 17A and 17B show the responses of the DNA-P(1)- and DNA-P(2)-functionalized devices, respectively, to DNA-T(1) and DNA-T(2). In both cases, complementary pairing results in an increase in as expected for a p-type device, while the noncomplementary negative controls show little change in signal, indicating a buffer with an optimal $\lambda_D$. The near-negligible signal of the negative controls indicates the $\lambda_D$ of about 3.3 nm effectively screens unbound DNA.

These results demonstrate the importance of selecting a buffer with an appropriate $\lambda_D$ to ensure proper NW-FET sensing. Careful control of the solution Debye length ($\lambda_D$) ensures that specific binding of macromolecules contribute to sensor response. An autonomous system for analyte detection must properly take these issues into account, such as employing ionic strength feedback control. This demonstration also profiles an application where charge distribution may enable unique measurements of the configuration of surface-bound species.

Figure 18:
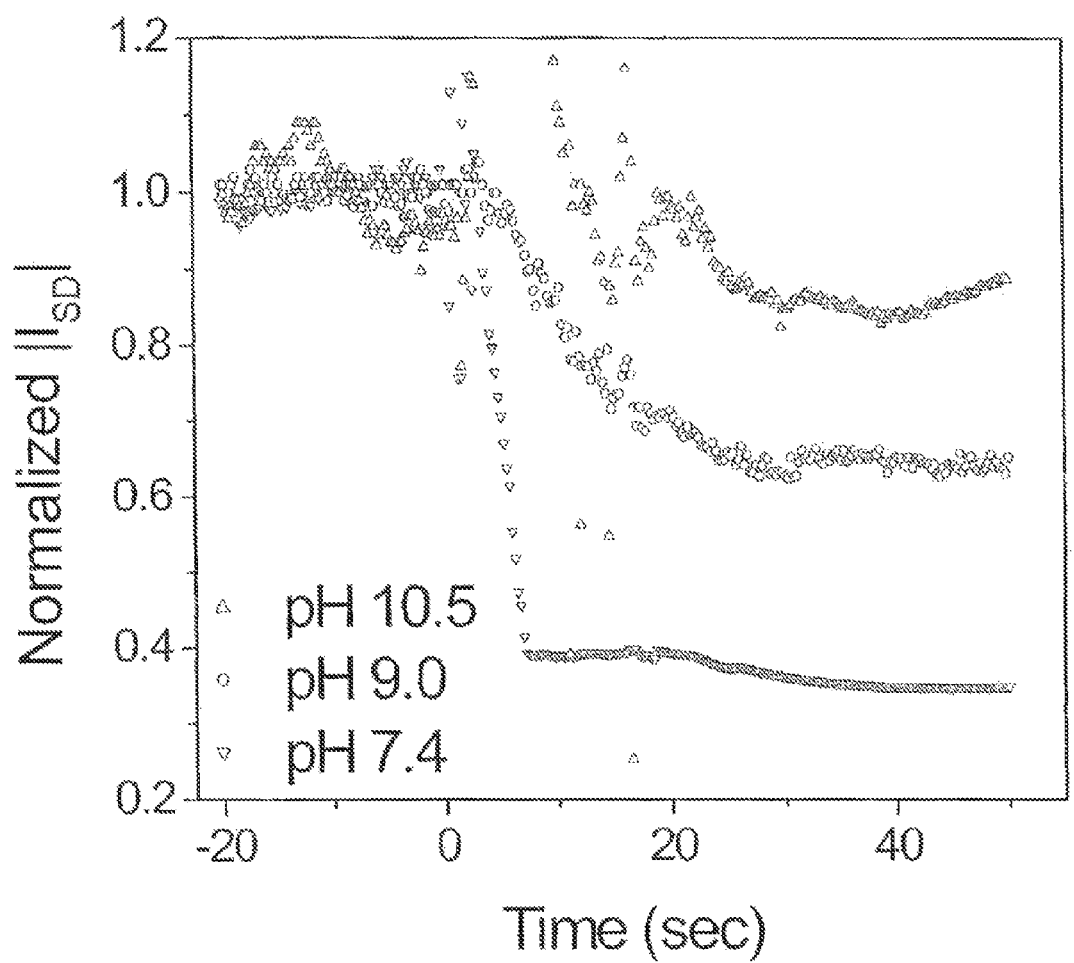
FIG. 18 is a graph demonstrating device sensitivity of biontin-functionalized p-type sensors to the addition of advin solutions with varying pH.

Protein sensing ability of the functionalized nano-sensor devices may be optimized with regard to its sensitivity to protein charge and concentration, according to another embodiment of the invention. This determination is made based on measured conductivity response resulting from the introduction of three solutions with varying pH to a biotinylated nano-sensor, where each solution includes 1 nM of avidin and an appropriate pH buffer. Even though avidin is positive in neutral solutions due to its high isoelectric point (pI about 10.5), its effective charge may be decreased by the increase in solution pH. FIG. 18 demonstrates decreased device sensitivity in correlation to increased solution pH. Hence, the value of $|pH_{solution}-pI|$ needs to be maximized to optimize protein sensing. In other implementations, protein sensing is optimized by the use of a linear solution pH gradient to determine unknown protein pIs.

In general, 0.1×PBS having pH of 7.4 may be utilized for biotin-streptavidin/avidin sensing, where the 0.1×PBS has a Debye screening length ($\lambda_D$) of about 2.2 nm. Despite the fact that calculating the actual amount of protein captured and sensed has inherent uncertainties, about 7 fg of protein is estimated to bind to a single sensor, assuming that the sensor has a cross-sectional width of about 100 nm and a cross-sectional thickness of about 40 nm, and the protein concentration is about 1 avidin molecule/25 nm$^2$. In addition, Biotinylation may be performed with N-hydroxysulfosuccinimide(sulfo-NHS)-biotin, sulfo-NHS-SS-biotin, or sulfo-NHS-LC-biotin (Pierce Chemical) at pH of 10.5.

Figure 19A:
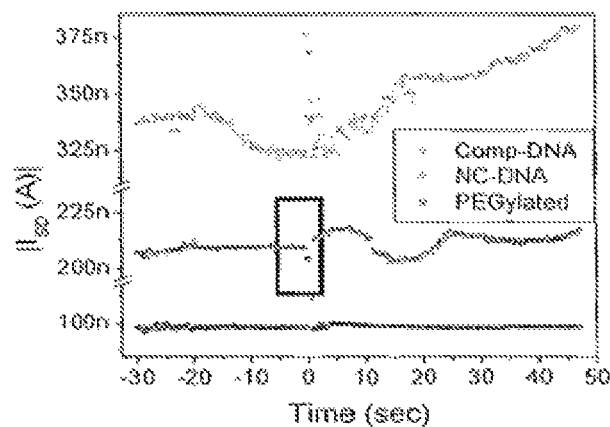
FIG. 19A is a graph demonstrating current responses in DNA-functionalized p-type sensors to the addition of a complementary and a non-complementary 15-mer concentration.

Selectively functionalized sensor devices may also be utilized in the detection of complementary DNA, as shown in FIG. 19A. In particular, two exemplary sensor devices are functionalized with a 20-mer, 5'-thiol ss-DNA, with subsequent introduction of either a complementary or a non-complementary 15-mer at a 100 fM concentration on each device. The sensor response to complementary strand addition is observed to be more than the non-complementary strand addition.

Figure 19B:
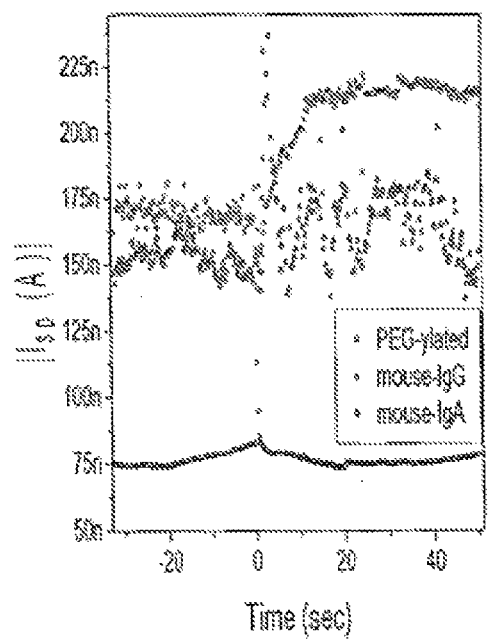
FIG. 19B is a graph demonstrating current responses in a goat-α-mouse IgG functionalized p-type sensor and a goat-α-mouse IgA functionalized p-type sensor to the introduction of mouse IgG and mouse IgA, respectively.
Figure 19C:
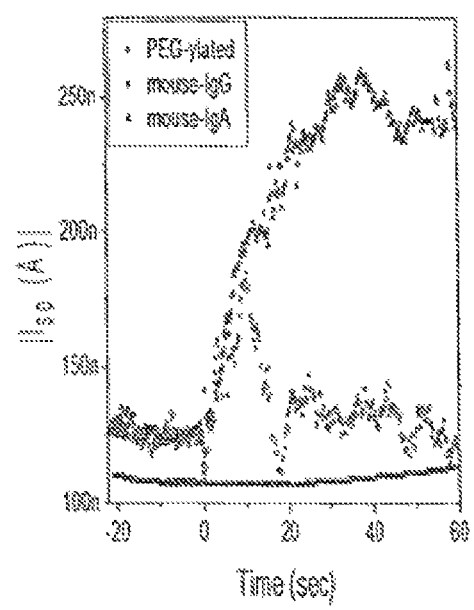
FIG. 19C is a graph demonstrating current responses in a goat-α-mouse IgG functionalized p-type sensor and a goat-α-mouse IgA functionalized p-type sensor to the introduction of mouse IgG and mouse IgA, respectively.

In another embodiment as shown in FIGS. 19B and 19C, a protein assay is performed by functionalizing two devices with goat-α-mouse IgG and two additional devices with goat-α-mouse IgA. One device from each group is used to sense the presence of mouse IgG and the other mouse IgA, where both solutions have about 100 fM concentrations. Sensing is subsequently performed at pH of 8.5 to maximize protein charge while maintaining protein conformation. As seen in FIGS. 19B and 19C, the appropriate ligand is detected in each case, while current in non-immune devices remained relatively constant. Thus, the ability of this functionalization approach for the detection of antibodies at less than about 100 fM concentrations is demonstrated. In certain examples, the captured antibodies are bound using NHS/ethylene dicarbodiimide coupling techniques. The sensing may be performed in a 1 mM sodium bicarbonate buffer, having pH of 8.4 and Debye screening length ($\lambda_D$) of about 6.8 nm.

The functionalized nano-wire sensors used in the aforementioned implementations may be nominally similar, with device cross-sectional thickness about 40 nm and device cross-sectional width varies from about 50 nm to about 150 nm.

Figure 6D:
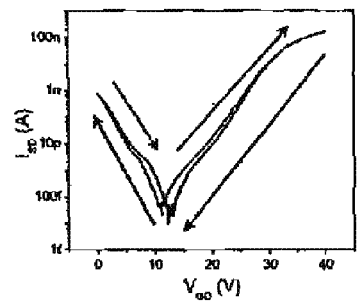
FIG. 6D is a graph of the source-drain current ($I_{SD}$) as a function of the gate-drain voltage ($V_{GD}$) for constant source-drain voltage for a forward and reverse sweep, indicated by the arrows, for the same n-type devices and suggests minimal defect-induced charge trapping in the n-type nano-wire sensor device.
Figure 6E:
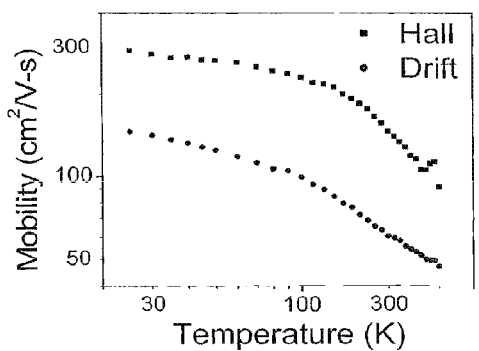
FIG. 6E is a graph depicting the drift and Hall mobilities for a p-type test structure.

According to another aspect of the invention, the nano-sensor devices, whether functionalized or unfunctionalized, are used for complementary sensing. N-type inversion-mode devices may be fabricated on the same wafer as p-type accumulation-mode devices to support the complementary sensing ability. An $I_{SD}$, ($V_{SD}$) dependence plot, with $V_{GD}$ varying from 0 to 40V in 1V increments, is shown in FIG. 6C for an exemplary n-type sensor device having a width of about 50 nm and a thickness of about 40 nm. The $I_{SD}$ ($V_{GD}$) dependence plot for $V_{SD}$=1V is shown in the inset of FIG. 6C. As with the p-type $I_{SD}$ ($V_{GD}$) behavior illustrated in FIG. 6A, the small hysteresis between forward and reverse $I_{SD}$ ($V_{GD}$) slopes in FIG. 6D suggests minimal defect-induced charge trapping in the n-type nano-wire sensor device. The observed n-type behavior is possibly due to the polarity of the contacts to the device, which may be controlled by contact implantation or physical definition. For simplicity, surface accumulation charge caused by RIE pattern definition may be used, which is sufficient to invert the contact, thereby decreasing the contact resistance and enabling inversion-mode behavior. This results in ambipolar behavior, as evident in the inset of FIG. 6C. The n-type and p-type nano-wire sensors may be incorporated into an integrated electronic system to perform functions such as on-chip signal processing, error detection, and complementary error detection for the purpose of avoiding false positives.

Figure 20A:
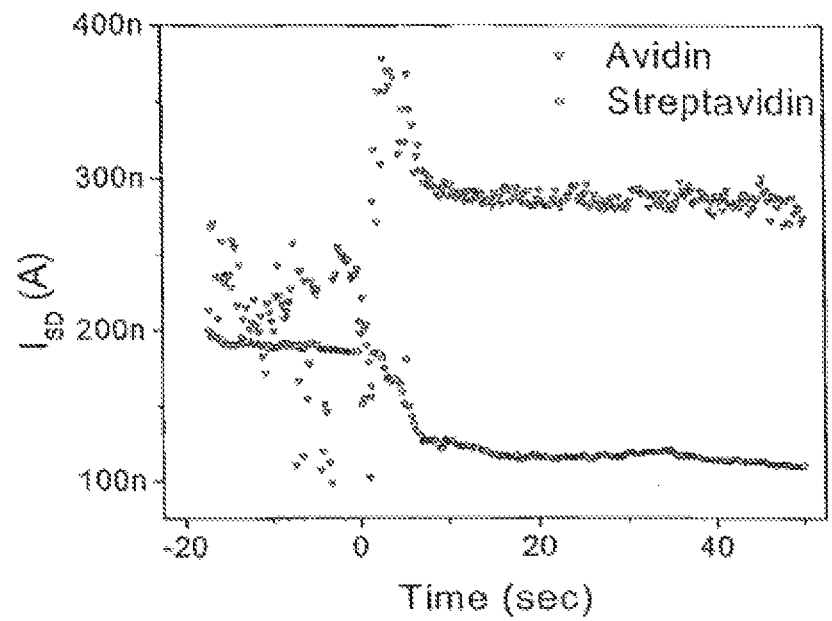
FIG. 20A is a graph illustrating conduction current responses in biotin-functionalized n-type sensors to the introduction of streptavidin and avidin.
Figure 20B:
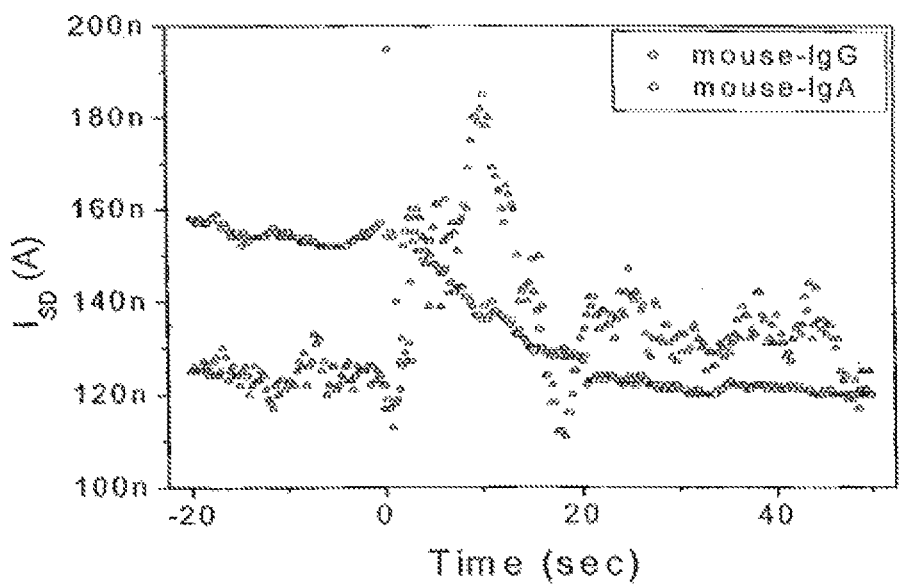
FIG. 20B is a graph illustrating current responses in a goat-α-mouse IgG functionalized n-type sensor to the addition of mouse IgG.

In certain embodiments, the response of a biotinylated n-type inversion-mode device to 1 nM streptavidin and avidin, introduced at time=0, is shown in FIG. 20A. These devices react with the opposite sense of the p-type accumulation-mode device shown in FIG. 15A. Additionally, two p-type nano-wire sensors are functionalized with goat-α-mouse IgG and demonstrate appropriately inverted and null responses to the presence of mouse IgG and mouse IgA, respectively. The mouse IgG and mouse IgA are at about 100 fM concentrations when introduced to the functionalized device at time t=0. The resulting conduction responses, as depicted in FIG. 20B, show opposite sense from the reaction of a p-type accumulation-mode device. Thus, the complementary sensing ability of the nano-wire sensors of the current invention has also been demonstrated for the detection of antibodies at less than about 100 fM concentration.

In certain implementations, measurements of current response may be taken at 0.25-second intervals with $V_{SD}$ and $V_{GD}$ held constant. For unfunctionalized sensor measurements, $V_{SD}$ may be set to −5V and $V_{GD}$ to −33V, while for functionalized sensor measurements, $V_{SD}$ may be set to −2V and $V_{GD}$ to −20V because research has shown that $V_{GD}$ of −20V is the optimal gate voltage. For implementations involving macromolecule addition, time=0 may be defined as the onset of protein/DNA addition. In addition, functionalization processes may run for about 100 seconds.

In certain exemplary configurations, a mixing device, such as the solution chamber of FIG. 6, is used to continuously mix solutions of interest after they are injected into a nano-sensor device. The volume of liquid in the solution chamber may be about 10 μL which includes 10 μL of buffer at the onset of each sensing run that is displaced by 100 μL of protein/DNA solution of which 10 μL remains.

The aforementioned nano-wire sensors also have important medical diagnostic applications. For example, the sensors may be used to differentiate between healthy cells and diseased cells based on monitoring of real-time cellular responses. The efficiency of this technique lays in its label-free detection approach according to which cells being tests for pathogens do not need to be tagged with any visualization beacons or labels. In addition, the smoothness of the active surfaces of the nano-wire sensors and their large surface-to-volume ratio make these sensors highly sensitive to bound molecular charges, hence enabling accurate and efficient detection of specific label-free reagents. Moreover, the crystalline semiconductor materials used to fabricate these sensors facilitate their seamless integration into any CMOS systems, particular as a part of molecular or cellular arrays for performing wide-scaling complementary error detection and integrated signal processing.

Ne-ELISA

The present invention also provides a novel method for both quantitative and qualitative protein sensing in solutions with physiologic salt concentrations. This embodiment utilizes enzymatic activity to overcome the critical Debye screening limitations associated with nanowire-FET sensing. Given the generality of this approach for protein sensing, sensitivity can be practically tuned by adjustment of the surface area available for protein binding or by choice of enzymes catalyzing solution ionic changes. Thus, the utility of this method is broad and durable, because it depends on the interplay between physical scaling of the devices and biochemical properties of the enzymes. This is in contrast to direct nanowire sensing, where sensitivity is solely dependent on device dimensions. Variations of this technology with different device architectures or enzyme choices can produce even more sensitive indirect nanowire sensors with fast response times operating in buffers with physiologic salt concentrations, which can benefit a wide variety of applications in biology and medicine.

According to another aspect of the present invention, the aforementioned sensors can be used as a nanoelectronic-enzyme linked immunosorbent assay (ne-ELISA), which combines the power of enzymatic conversion of bound substrate with electronic detection. This configuration can produce a local enzyme-mediated pH change proportional to bound ligand concentration. For example, nanowire-enzyme FETs configured as pH sensors can be used for quantitative and qualitative detection of specific compounds, such as interleukin-2 (IL-2), in physiologically buffered solution. Using calibrated device responses to pH changes, sensitivity for quantitative detection of IL-2 concentrations can be demonstrated down to about 3 pg/mL. By successfully bypassing the Debye screening inherent in physiologic fluids, the ne-ELISA provides wide applicability for ligand detection in a range of relevant solutions. While the various examples described herein relate to detection of cytokines, the ne-ELISA may be used without limitation to detect any sort of compound, such as proteins or nucleic acids, synthetic compounds or any other sort of compound that can be specifically bound by a receptor molecule.

The present invention thus includes a method that affects a solution pH change upon specific ligand binding. As depicted in FIG. 21, this approach is similar to an enzyme linked immunosorbent assay (ELISA), but correlates protein presence with an enzyme-induced pH increase rather than the traditional colorimetric change. Increasing pH deprotonates surface hydroxyl groups on the nanosensors, resulting in a net decrease in positive gate charge and, in turn, a decrease in channel current for n-type devices. For example, by monitoring a urease-induced pH increase, the quantity of bound protein is calculated, in a configuration that eliminates concerns over Debye screening in high-salt buffers and nanowire-specific functionalization schemes and in a format that can be adapted for use in a variety of settings from the bench to the clinic.

In one embodiment, the sensor for performing the ne-ELISA includes a semiconductor layer formed in or on a substrate, and a channel having nano-scale cross-sectional dimensions formed in the semiconductor layer and forming an electrically conducting pathway between a first and second contact. The channel also includes at least one exposed lateral face. Also included is a reservoir for holding a solution to be tested for the potential presence and quantity of a specific compound. As contemplated herein, any of the aforementioned sensors and their fabrications described elsewhere herein can be employed for ne-ELISA sensing.

The sensor is functionalized with a first receptor that is suitable for binding a specific compound in the solution to be tested. For example, the first receptor may be an antibody, such as a polyclonal antibody, or even a monoclonal antibody that is specific for the targeted compound of interest to be detected. It should be understood that any sort of molecule can be used for the first receptor, provided such molecule specifically binds to the targeted compound. The first receptor can be attached, such as by conjugation for example, to at least a portion of the semiconductor layer or any of the lateral faces, such that the receptor may specifically bind to the particular compound. Functionalizing the sensor in this manner should not encompass the entire sensor surface area, but should leave enough surface area on the sensor unfunctionalized (as explained previously above) such that the sensor can still effectively determine any change in charge of the solution.

A second receptor that is also suitable for binding the specific compound is used to bind the specific compound while it is also bound to the first receptor. This second receptor may also be an antibody, such as a monoclonal antibody, or any other sort of molecule capable of specific binding to a targeted compound in solution. The second receptor is also attached to an enzyme, such as urease. While any enzyme may be used, the enzyme chosen should be based on its ability to convert a substrate that can alter the charge of the solution when that substrate is added to the solution and subsequently converted. For example, if urea is used as a hydrolysable substrate, a urease should be attached to the second receptor.

According to another aspect of the present invention, a method for determining the presence of a compound in a solution is provided via utilization of any one of the aforementioned ne-ELISA sensors. The steps of the method can include: a) attaching a first receptor that is suitable for binding a specific compound in the solution onto at least one exposed surface of any type of sensor described herein; ii) adding the solution to the reservoir of the sensor; iii) adding to the solution a second receptor that is suitable for binding the specific compound while the specific compound is also bound to the first receptor, and where the second receptor is also attached to an enzyme; iv) adding to the solution a second compound that is a substrate for the enzyme; and v) measuring an electrical property in the sensor before and after the application of the second compound. Any measured difference would be indicative of the presence of the specific compound in the solution being tested. It should be understood by those skilled in the art that because the ne-ELISA is based on the enzymatic conversion of a substrate, that various wash steps, as described in the following experimental examples, should be performed to insure sensor accuracy and sensitivity to any minute changes in charge.

Experimental Examples

In one embodiment, indium oxide nanowires were used. These nanowires were grown by the laser-ablated hot-wall chemical vapor deposition method using a gold catalyst. Devices were fabricated on 2-inch wafers with a global backgate, and contacts to the nanowires were defined with a nickel/gold (Ni/Au) stack. After preliminary screening, wafers were diced and functionalized as shown in FIG. 21B. This scheme was designed to solely functionalize the gold leads due to thiol-mediated self-assembled monolayer (SAM) formation. Thus, surface hydroxyl groups on the indium oxide nanowires was maintained and available for protonation and deprotonation necessary for measuring solution pH.

Samples were first treated with Ω-mercaptocarboxylic acid (FIG. 21B-i) to confer carboxylic acid functionality to the gold leads. Gold leads contacting the nanowires were used for convenience; however, any exposed gold surface in proximity to the sensor could be utilized. The alkane chain in the Ω-mercaptocarboxyclic acid also insulates the gold surface from the solution. This passivation was demonstrated using cyclic voltametery. As depicted in FIG. 22, the redox peaks due to the exposed gold surface are significantly reduced after functionalization, indicating the formation of a complete SAM and, thus, a functional surface.

Self-assembled monolayer formation on the gold leads minimally affects the electrical properties of the indium oxide nanowires. This was shown in the pre- and post-functionalization dependence of drain-source current on drain-source voltage [$I_{DS}$ ($V_{DS}$)] for varying gate-drain voltage ($V_{GD}$) depicted in FIG. 23. The insets show the $I_{DS}$ ($V_{GD}$) dependence for the $V_{DS}$=0.5V operating point used in all sensing experiments described herein. The post-functionalization characteristics show that SAM formation only slightly decreases the threshold voltage ($V_t$, thus increasing $I_{DS}$ for a set $V_{GD}$ in post-functionalized devices). Additionally, the subthreshold leakage current was also slightly increased, but to a level of about 100-fold lower than that used for sensing.

Figure 24A:
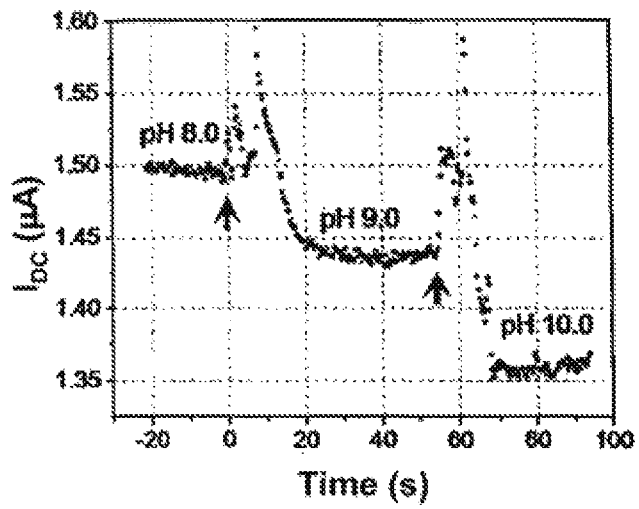
FIG. 24A is a graph depicting device response to unit changes in pH. For time<0, a pH 8.0 buffer was present in the reservoir. At time=0 this buffer was exchanged with a buffer at pH 9.0 and at time=57.25 s a second exchange, with a pH 10.0 buffer, was performed. All buffers were 0.01×PBS with 150 mM NaCl and were titrated using NaOH and HCl.

First, the pH sensitivity of the $In_2O_3$ NWs was characterized. Conventional indium tin oxide ISFETs have been previously demonstrated to have a linear pH sensitivity between pH 2 and 12, thus undoped $In_2O_3$ was expected to exhibit a similar response. The response of a characteristic device to changes in pH, achieved by completely exchanging the sensing reservoir with buffers of different pH (pH=8.0 initially, and pH=9.0 and 10.0, at times=0 and 57.25 s, respectively), is shown in FIG. 24A. The operating point for this device was $V_{DS}$=1 V and $V_{GD}$=0V. The $I_{DS}$ of the n-type $In_2O_3$ NWs decreased with increasing pH due to the decreasing degree of protonation of the surface hydroxyl groups. Fluid injection induced transients that settled to a steady state within about 20 s. Devices responded linearly to unit steps in pH in about the pH 8-10 range.

Figure 24B:
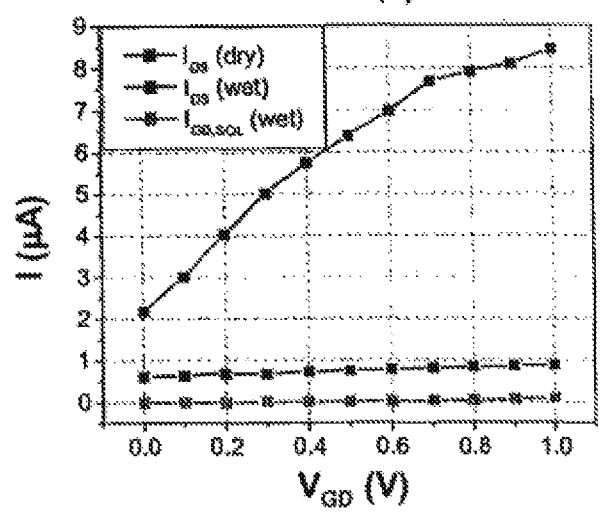
FIG. 24B is a graph depicting $I_{DS}$ vs. $V_{GD}$ dependencies for a single device when backgated and solution-gated. Solution gating was performed in the pH 8.0 buffer described in the text. The green dataplot shows the leakage current of the device ($I_{GD}$,SOL) during the solution-gating measurement.
Figure 24C:
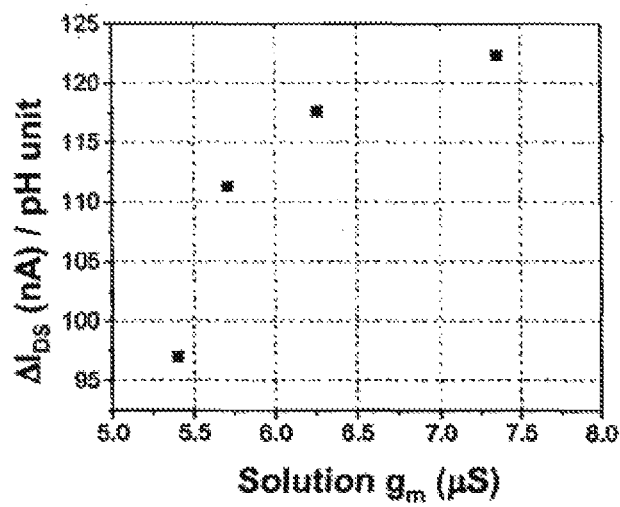
FIG. 24C is a graph depicting a scatter plot of the Δ $I_{DS}$/pH unit response vs. the solution transconductance ($g_m$) values for four $In_2O_3$ nanowire devices. The $R^2$ value of the linear fit described in the text is 0.75.

To accurately calibrate device pH response, transconductance ($g_m$) was measured while devices were immersed in solution. This is termed the solution transconductance. To create a reservoir for fluid handling, a poly(dimethylsiloxane) (PDMS) gasket capable of holding ~4 µL was placed over the die. Gating of the device was achieved through the solution by submerging gate and reference electrodes into the buffer (the drain and reference electrodes were connected). FIG. 24B illustrates the transconductances obtained by backgating and solution-gating a single, representative device. The solution-gated device transconductance was greater than backgated value due to the remote backgate. The device-to-solution leakage current ($I_{GD}$,SOL, FIG. 24B) remained two orders of magnitude below the device current ($I_{DS}$) for $V_{GD}$<0.8 V. Thus, to calculate solution $g_m$, a linear best fit was made to the solution-phase $I_{DS}$ vs. $V_{GD}$ plot for 0.1 toreq. $V_{SD}$.1 toreq.0.8 V. Device sensitivity showed a clear correlation between increasing pH and solution $g_m$, demonstrated in FIG. 24C for four different devices. A linear fit to these data yielded a trendline that was within about a 6.7% error of the value of each $I_{DS}$/ΔpH datapoint. Device sensitivity could thus be calculated by dividing ΔI/pH unit by the solution $g_m$. The average sensitivity of the four devices shown in FIG. 24C was 18.2.+−.1.2 mV/pH unit, a value below the maximum sensitivity of an ion sensitive FET, which is the ideal Nernst potential of 58 mV/pH unit.

In an exemplary embodiment of the present invention, neutravidin, a tetravalent biotin-binding protein, was used to demonstrate a ne-ELISA and its capacity for sensing. First, carboxylic acid groups were converted to biotin moieties through the use of biotin-LC-hydrazide (FIG. 21C-i). A poly(dimethylsiloxane) (PDMS) gasket was then placed over each die (not shown) to create a reservoir for fluid handling that holds about 4 µL. In order to prevent nonspecific protein adsorption to the chip and reservoir sidewalls, the sensor was treated with a blocking solution of bovine serum albumin (BSA), a typical procedure used in conventional calorimetric ELISA protocols to minimize non-specific binding. Neutravidin, which binds the biotinylated leads, was then added at about a 100 ng/mL concentration (FIG. 21C-ii). In the final step, biotinylated urease was bound to the surface-bound neutravidin (FIG. 21C-iii).

Figure 21A:
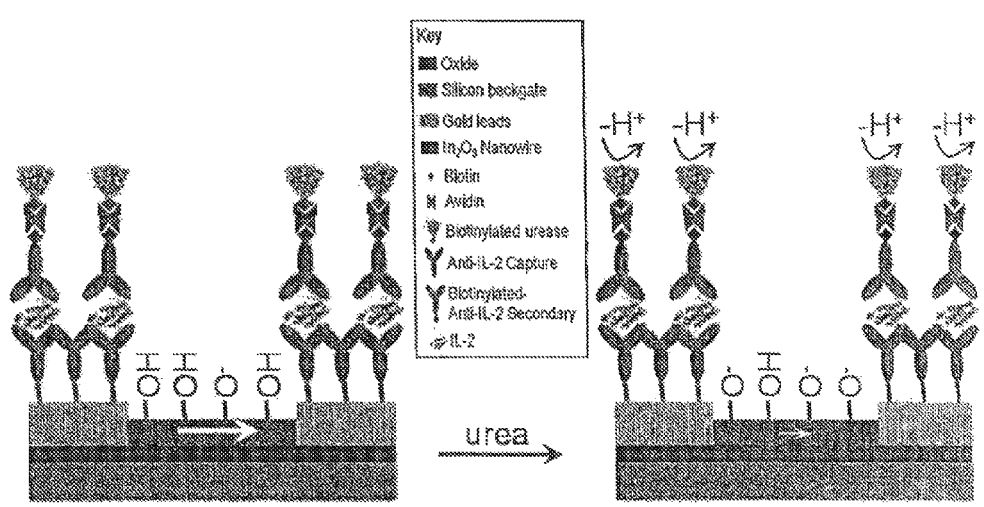
FIG. 21A is a schematic of the ne-ELISA approach. Before the addition of urea, the indium oxide surface is relatively protonated, inducing a relatively large channel current (large white arrow). The addition of urea results in the removal of protons from the solution and, thus, increased deprotonation of the nanowire surface. This, in turn, induces a decrease in channel current (small white arrow).
Figure 21B:
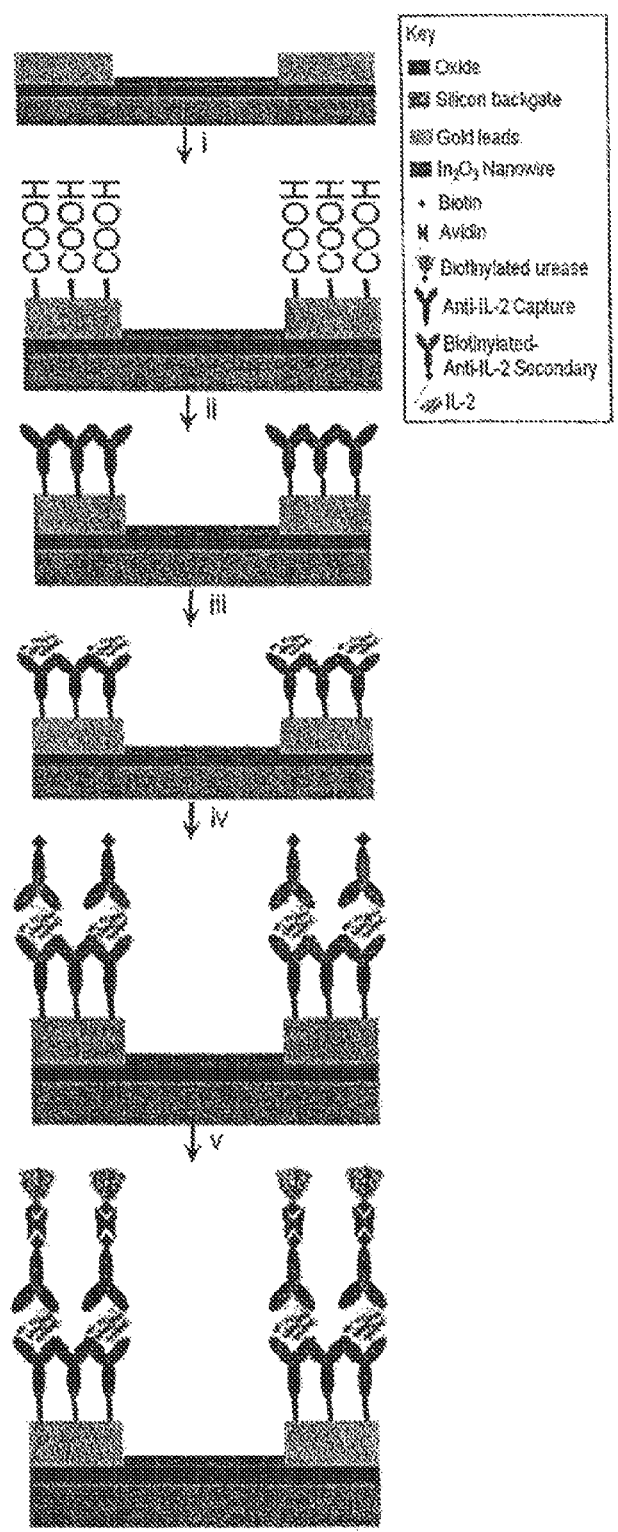
FIG. 21B is a schematic of a surface functionalization embodiment.
Figure 21C:
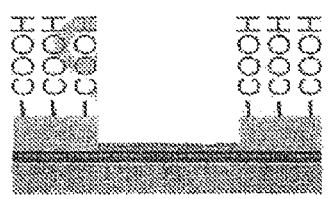
FIG. 21C is another schematic of a surface functionalization embodiment.
Figure 22:
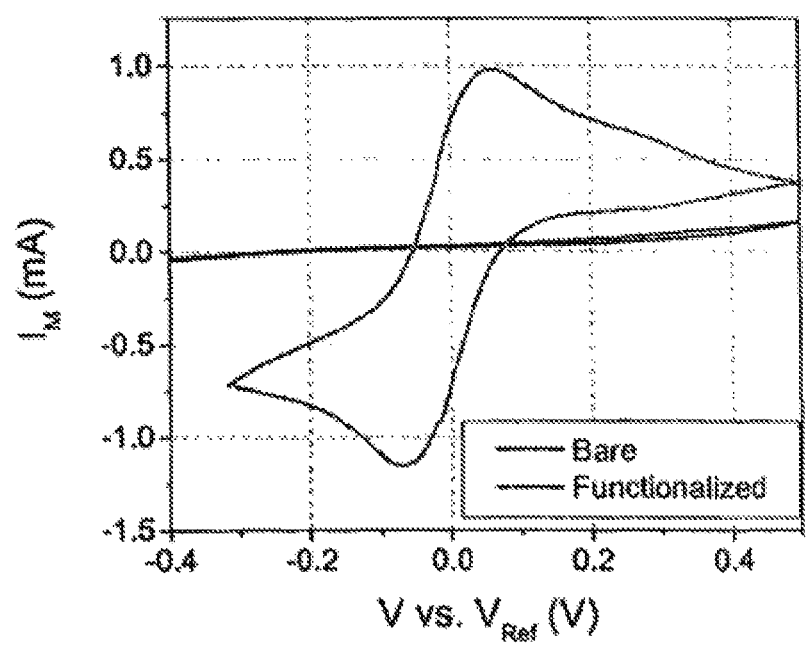
FIG. 22 is a graph depicting a cyclic voltammogram for an unfunctionalized (bare) and HS—$(CH_2)_n$—COOH functionalized device demonstrating passivation of the Au leads. The solution is 50 mM $Fe^{2+}/Fe^{3+}$ in 0.1 M KCl. Five sweeps were performed at 100 mV/s and the fifth is shown for each device.
Figure 23A:
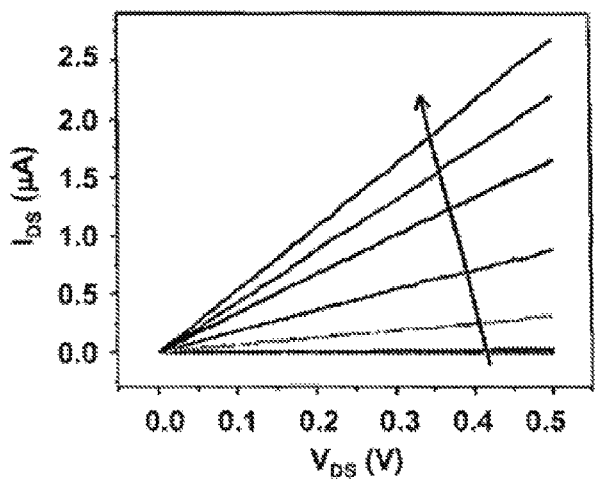
FIG. 23A is a graph depicting unfunctionalized $I_{DS}$ ($V_{DS}$) characteristics for $V_{GD}$ increased from −25V to 25V in 5V increments for a single representative. The arrow shows increasing $V_{GD}$.
Figure 23B:
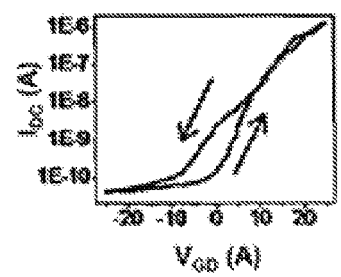
FIG. 23B shows the $I_{DS}$ ($V_{GD}$) characteristics for $V_{DS}$=0.5V for the same device and the arrows indicate the sweep direction. The operating point for sensing measurements was $V_{DS}$=0.5V and $V_{GD}$=0V.
Figure 23C:
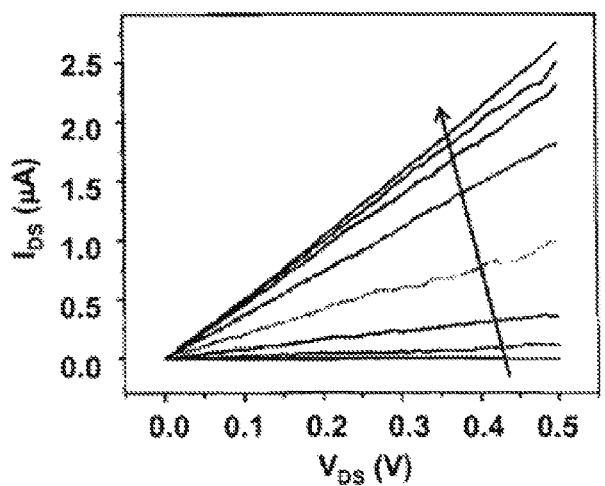
FIG. 23C is a graph depicting functionalized [HS—$(CH_2)_n$—COOH] $I_{DS}$($V_{DS}$) characteristics for $V_{GD}$ increased from −25V to 25V in 5V increments for a single representative. The arrow shows increasing $V_{GD}$.
Figure 23D:
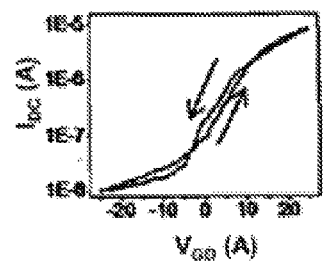
FIG. 23D shows the $I_{DS}$ ($V_{GD}$) characteristics for $V_{DS}$=0.5V for the same device and the arrows indicate the sweep direction. The operating point for sensing measurements was $V_{DS}$=0.5V and $V_{GD}$=0V.

The principle of the ne-ELISA is illustrated schematically in FIG. 21A. Urease hydrolyzes urea according to the following reaction:

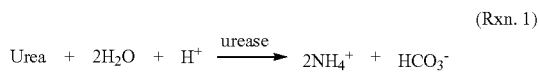

(Rxn. 1)

Thus, upon addition of urea to the reservoir containing bound urease, the solution pH would rise, thereby decreasing $I_{SD}$. Assuming urea was added at a sufficient concentration for the urease to operate at its maximum speed ($V_{max}$), the rate of pH change would depend on the amount of urease present in the reservoir. An excess of all protein solutions could be used (except for ligands), and thus the rate of pH change would be directly proportional to the quantity of these proteins bound to the leads.

Sensing measurements were performed in about 1 mM phosphate buffer at an initial pH=8.0. A weak buffer was used to allow enzymatically-produced solution pH changes to occur. The reservoir was filled half way (about 2 µL) with this buffer and devices were stabilized for about 5-10 min under active measurement conditions ($V_{DS}$=0.5V, $V_{DG}$=0V). This equilibration time was required for the channel current ($I_{DS}$) to reach a steady state and is similar to that required for the elimination of initial background current in conventional ISFET glucose sensors. During sensing measurements, about 2 µL of a 0.1 M urea solution in the same pH 8.0 buffer was manually added with a micropipette tip and the solution was mixed by pipetting up-and-down for ~5-10 sec, after which time the micropipette tip was removed.

Figure 21D:
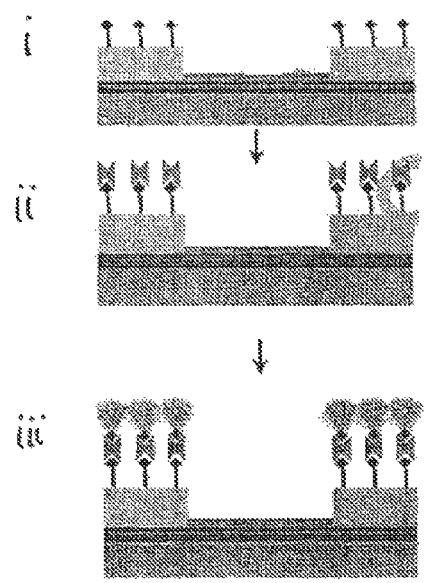
FIG. 21D is a graph illustrating the response [$I_{DS}$ (time)] of the sensor configured for avidin detection to the addition of urea. Time=0 denotes the addition of the urea solution.
Figure 21D:
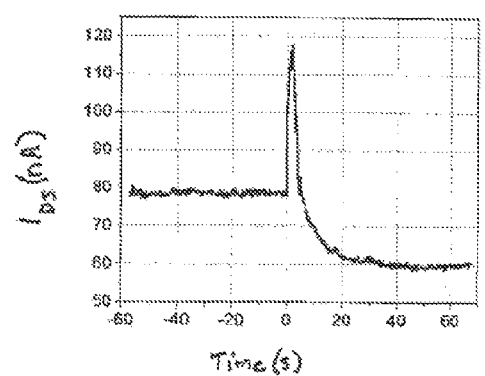

The response of the device configured for neutravidin sensing is illustrated in FIG. 21D. The urease-catalyzed pH increase resulted in a decrease in $I_{DS}$. Channel current stabilization after ~40 sec was most likely due to the pKa=9.2 of the ammonium ion, the solution buffering activity, and the decrease of urease activity at high pH. In order to estimate the quantity of bound protein, pH sensitivity was calculated by multiplying the (dry) functionalized (SAM-only) device transconductance around $V_{DG}$=0V, 217 nA/V, by the Nernst potential, 58 mV/pH.

$$\left( g_m, \frac{\partial I_{DS}}{\partial V_{DG}} \bigg|_{V_{DS}} \right)$$

The response of this device was ~12.7 nA/pH unit, assuming an insignificant transconductance change between dry and fully functionalized solution-phase conditions. In addition, the assumption was made that the Nernst potential is equivalent to the gate potential, such that it accurately described the FET response of a nanowire. Conventional indium tin oxide ISFETs have been previously demonstrated to have a linear pH sensitivity between pH 2 and 12, thus it was expected that undoped indium oxide should exhibit a similar response. The ~18.3 nA current decrease in FIG. 21D therefore suggests a pH increase of about 1.4 units, reasonable given the pKa of the ammonium ion. Converting to proton concentration using the definition of pH, $$pH = -\log([H^+])$$ (1)

yielded a [H⁺] decrease of about $9.6 \times 10^{-9}$ M. According to Rxn. 1, a mol of protons was lost for each mol of urea hydrolyzed (the bicarbonate ion, pKa=3.2, should be fully dissociated at pH 8.0); thus, the concentration of hydrolyzed urea must also be about $9.6 \times 10^{-9}$ M. In the 4 µL reservoir, this corresponded to about $3.8 \times 10^{-14}$ mol.

The unit activity for jack bean urease used in these experiments was given as about 100 mol urea hydrolyzed/min/mg urease. Accounting for the 40 second time required for the device to reach a steady-state (FIG. 21D) gave about $6.7 \times 10^{-5}$ mol urea hydrolyzed/mg urease. Thus, a urease quantity of about $5.8 \times 10^{-10}$ mg was obtained. As described above, this mass should be equivalent to that of the added neutravidin, with a factor no greater than about three, due to the four biotin binding sites per neutravidin molecule. Assuming a 2:1 urease-to-neutravidin ratio and again accounting for the reservoir volume yielded about a 72.5 ng/mL neutravidin concentration, in good agreement with the 100 ng/mL concentration of neutravidin added.

In another embodiment, the capability of the ne-ELISA for detection of labile macromolecules was demonstrated by the detection of cytokine interleukin-2 (IL-2), whose presence reports on the activity of the T cell immune response. In the initial step, the a capture monoclonal antibody against IL-2 was conjugated or otherwise attached to the carboxylic groups on the gold leads through its N-terminus (FIG. 21B-ii). This was followed by a wash step that removed unbound capture antibody (all binding steps described below were followed by washes) and the subsequent placement of a PDMS gasket over the nanowire devices to create the sensing reservoir. Next, a bovine serum albumin solution was used to prevent nonspecific protein adsorption to the chip and reservoir sidewalls, a typical blocking step used in conventional colorimetric ELISA protocols to minimize non-specific binding. This was followed by the addition of IL-2 at varying concentrations (across different devices) to the reservoir (FIG. 21B-iii). A secondary, biotinylated antibody to IL-2 was then introduced (FIG. 21Bb-iv), followed by the addition of neutravidin, a tetravalent biotin-binding protein, and biotinylated urease (FIG. 21B-v). In this example, the rate of change in $I_{DS}$ correlated directly with the quantity of bound urease and, in turn, bound IL-2.

Figure 25A:
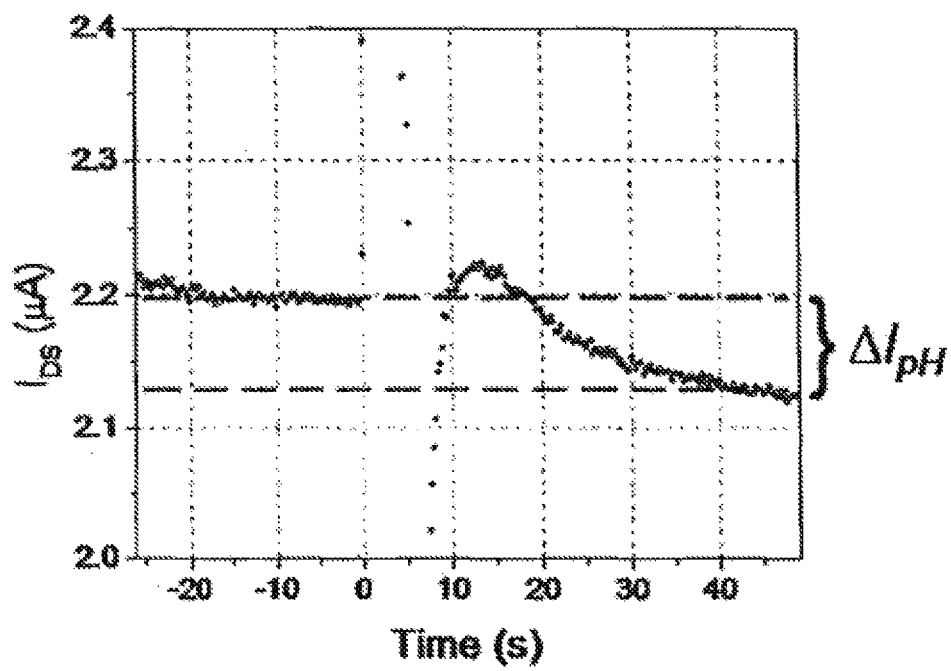
FIG. 25A is a graph depicting a response [$I_{DS}$ (time)] of the sensor configured for IL-2 detection with 25 pg/mL IL-2 present during the protein-binding step (FIG. 21b). At time=0 the 100 μM urea solution was added to the pH 8.0 buffer. For this device, $\Delta I_{pH}$=68.0 nA. The dashed lines show the initial and final $I_{DS}$ levels, respectively.
Figure 25B:
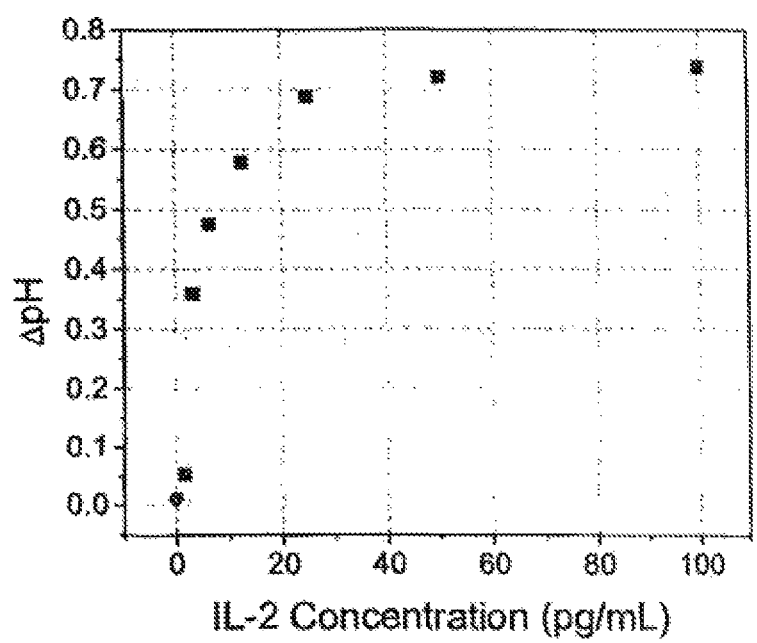
FIG. 25B is a graph depicting a plot of the ΔpH measured by eight devices vs. the IL-2 concentration incubated with each sensor. The device shown as a circle was the control, to which no IL-2 was added during the protein-binding step (FIG. 21b).

Operation of the ne-ELISA is demonstrated in FIG. 25B. The reservoir was about half filled (2 µL) with the sensing buffer (0.01.times. phosphate buffered saline, PBS, plus 150 mM sodium chloride) at an initial pH=8.0. Devices were stabilized for 5-10 min under active measurement conditions ($V_{DS}$=0.5V, $V_{GD}$=0V). This equilibration time was required for the channel current ($I_{DS}$) to reach a steady state and was similar to that required for the elimination of initial background current in conventional ISFET glucose sensors. During sensing measurements, about 2 µL it of a 100 µM urea solution in the same pH 8.0 buffer was manually added with a micropipette and the solution was mixed by micropipette mixing for ~5-10 s. Introduction of this solution occurred at time=0 in all figures. The response of a device to the presence of about 12.5 pg/mL solution of IL-2 is depicted in FIG. 25A. The decrease in $I_{DS}$ and its continued negative derivative indicated that the addition of the urea solution resulted in a continuous drop in pH throughout the course of the measurement. The key detection parameter was the asymptotic current difference ($\Delta I_{pH}$), calculated by subtracting $I_{DS}$ (time>40 s) from $I_{DS}$ (time<0 s), thus the transient current spikes observed during urea addition and subsequent mixing did not interfere with the assay. For the device depicted in FIG. 25A, $\Delta I_{pH}$=68.0 nA. To demonstrate that this decrease in $I_{DS}$ was due to urease activity and not to addition of the urea solution, a control device without bound urease was used. Upon introduction of the urea solution, a decrease of about 1.8 nA in $I_{DS}$ was observed ($\Delta I_{pH}$=1.8 nA), setting this value as the lower sensitivity limit for the assay.

Detection sensitivity of the ne-ELISA was determined by treating devices with decreasing concentrations of IL-2. Device responses to six serial dilutions of IL-2 was measured, starting with a concentration of about 100 pg/mL (the median concentration, about 12.5 pg/mL, is depicted in FIG. 25A). The responses of the seven devices were converted into ΔpH changes by fitting the solution transconductance values of the devices (determined as described above after sensing measurements were completed) to the trendline determined from the control devices in FIG. 24C. These data were plotted in FIG. 25B and demonstrated the sensitivity of the assay for the low IL-2 concentrations relevant for T cell stimulation. The detectable range of the assay was between a maximum determined by the surface area of the gold leads and a minimum dictated by device sensitivity as well as lead surface area. Thus, by increasing the gold surface area, the sensitivity range of the ne-ELISA was significantly improved. However, the maximum sensitivity could not be increased above an upper limit that exists due to the pKa of the ammonium ion, as well as the decrease in urease activity at high pH, although this limitation may be overcome through a different choice of enzymatic substrate.

The foregoing description of the preferred embodiment of the invention has been presented for the purposes of illustration and description. It is not intended to be exhaustive or to limit the invention to the precise form disclosed. Many modifications and variations are possible in light of the teaching herein.

We claim:

1. A device for determining the presence of a specific compound in a solution, comprising:
    a semiconductor layer formed in or on a substrate;
    a channel having nano-scale cross-sectional dimensions formed in the semiconductor layer and forming an electrically conducting pathway between a first and a second contact, wherein the channel includes at least one exposed lateral face;
    a first receptor, suitable for binding the specific compound in the solution, attached to the nano-scale channel having at least one exposed lateral face, wherein only the exposed lateral face or faces is functionalized; and
    a reservoir for holding the solution;
    wherein the solution comprises a second receptor that is suitable for binding the specific compound when the specific compound is bound to the first receptor, wherein the second receptor is attached to an enzyme;
    wherein, when the solution having the second receptor is added to the device, and a second compound that is a substrate for the enzyme is subsequently added to the solution, a measured difference in an electrical property in the device before and after the application of the second compound is indicative of the presence of the specific compound in the solution.

2. The device of claim 1, wherein the enzyme is urease and the second compound is urea.

3. The device of claim 1, wherein the specific compound is a cytokine.

4. The device of claim 3, wherein the specific compound is an interleukin or an interferon.

5. The device of claim 1, wherein the first receptor is a monoclonal antibody.

6. The device of claim 1, wherein the reservoir is a microfluidic channel or a batch reservoir.

7. The device of claim 1, wherein the channel has a trapezoidal, square, round, ovoid, or rectangular cross-section.

8. The device of claim 7, wherein the first and second contact form a source and a drain contact, respectively, and a gate contact is applied on a top surface of the channel.

9. The device of claim 7, wherein the semiconductor layer is p-type.

10. The device of claim 7, wherein the semiconductor layer is n-type.

* * * * *

UNITED STATES PATENT AND TRADEMARK OFFICE
CERTIFICATE OF CORRECTION

PATENT NO. : 9,921,216 B2
APPLICATION NO. : 14/755615
DATED : March 20, 2018
INVENTOR(S) : Tarek M. Fahmy et al.

Page 1 of 1

It is certified that error appears in the above-identified patent and that said Letters Patent is hereby corrected as shown below:

In the Specification

Column 1, Lines 19-33, replace:
"STATEMENT REGARDING FEDERALLY SPONSORED RESEARCH OR DEVELOPMENT
This invention was made, in part, using funds obtained from the U.S. Government ARO, WF-11NF-08-1-0365 and NIH RO1 (EB008260). The U.S. Government also has a paid up license in this invention and the right in limited circumstances to require the patent owner to license others on reasonable terms as provided by the terms of Contract Nos. ONR K00134, AFOSR L00084, and AFOSR R06868 and graduate student fellowships that are supplied by the Department of Homeland Security and the National Science Foundation. The U.S. Government therefore has certain rights in the invention."

With:
--STATEMENT REGARDING FEDERALLY SPONSORED RESEARCH
This invention was made with government support under EB008260 awarded by National Institutes of Health and under W911NF-08-1-0365 awarded by US Army Research Office and under N66001-04-1-8902 awarded by Space and Naval Warfare Systems Command. The government has certain rights in the invention.--

Signed and Sealed this
Eighteenth Day of June, 2019

Andrei Iancu
*Director of the United States Patent and Trademark Office*